(12) United States Patent
Okkel et al.

(10) Patent No.: US 10,544,091 B2
(45) Date of Patent: *Jan. 28, 2020

(54) REACTION PRODUCTS CONTAINING AMIDOAMINE GROUPS

(71) Applicant: BYK-Chemie, GmbH, Wesel (DE)

(72) Inventors: Andreas Okkel, Wesel (DE); Bernd Göbelt, Wesel (DE); Jürgen Omeis, Dorsten-Lembeck (DE); Jörg Bömer, Wesel (DE); Monika Roch, Dinslaken (DE); Sabine Stelz, Öberhausen (DE)

(73) Assignee: BYK-Chemie, GmbH, Wesel (DE)

( * ) Notice: Subject to any disclaimer, the term of this patent is extended or adjusted under 35 U.S.C. 154(b) by 0 days.

This patent is subject to a terminal disclaimer.

(21) Appl. No.: 15/575,128

(22) PCT Filed: Jun. 3, 2016

(86) PCT No.: PCT/EP2016/062719
§ 371 (c)(1),
(2) Date: Nov. 17, 2017

(87) PCT Pub. No.: WO2016/193474
PCT Pub. Date: Dec. 8, 2016

(65) Prior Publication Data
US 2018/0141896 A1    May 24, 2018

(30) Foreign Application Priority Data
Jun. 3, 2015 (EP) .................... 15170609

(51) Int. Cl.
*C07C 237/04* (2006.01)
*C08G 18/76* (2006.01)
*C07C 269/02* (2006.01)
*C07C 271/28* (2006.01)
*C08G 18/71* (2006.01)
*C09D 5/00* (2006.01)
*C09D 133/00* (2006.01)
*C08G 18/28* (2006.01)
(Continued)

(52) U.S. Cl.
CPC .......... *C07C 237/04* (2013.01); *C07C 269/02* (2013.01); *C07C 271/26* (2013.01); *C07C 271/28* (2013.01); *C08G 18/283* (2013.01); *C08G 18/284* (2013.01); *C08G 18/289* (2013.01); *C08G 18/2815* (2013.01); *C08G 18/2825* (2013.01); *C08G 18/2835* (2013.01); *C08G 18/71* (2013.01); *C08G 18/711* (2013.01); *C08G 18/718* (2013.01); *C08G 18/7621* (2013.01); *C09D 5/00* (2013.01); *C09D 7/45* (2018.01); *C09D 7/65* (2018.01); *C09D 17/00* (2013.01); *C09D 133/00* (2013.01)

(58) Field of Classification Search
None
See application file for complete search history.

(56) References Cited

U.S. PATENT DOCUMENTS 4,032,698 A    6/1977  Ashe
4,101,529 A    7/1978  Ammons
(Continued)

FOREIGN PATENT DOCUMENTS

CA    2 201 845 C    11/2004
DE    697 10 935 T2   10/2002
(Continued)

OTHER PUBLICATIONS

Wang et al. Yaoxue Xuebao , 2011, 46(1), 102-108.*
(Continued)

*Primary Examiner* — Ana Z Muresan
(74) *Attorney, Agent, or Firm* — Curatolo Sidoti Co., LPA; Joseph G. Curatolo; Salvatore A. Sidoti

(57) ABSTRACT

A reaction product containing amido amine groups, comprising one or more species of the general formula (I)

$$(R^1\text{—}X)_p\text{—}Z^1\text{—}(XH)_y \quad (I)$$

where p+y=w and w is an integer from 1 to 10, p is an integer from 1 to 10, y is an integer from 0 to 9, and X is independently O, NH and/or $NZ^2$ and XH is independently a hydroxyl group OH, a primary amino group $NH_2$ and/or a secondary amino group $NHZ^2$ where $Z^2$ is independently a branched or unbranched, saturated or unsaturated organic radical $G(U)_a$ where U is independently a hydroxyl group, a primary amino group or a secondary amino group and a is an integer from 0 to 9, where p+y+a≤10, and G is a branched or unbranched, saturated or unsaturated organic radical, the p $R^1$ radicals are independently a radical of the general formula (II)

$$Y\text{—}O\text{—}CO\text{—}NH\text{—}R^2\text{—}NH\text{—}CO \quad (II)$$

in which the p Y radicals are independently a branched or unbranched, saturated or unsaturated organic radical which has 1 to 1000 carbon atoms and does not contain any hydroxyl groups, any primary amino groups or any secondary amino groups, the p $R^2$ radicals are independently a branched or unbranched, saturated or unsaturated organic radical having 6 to 20 carbon atoms, $Z^1$ is a branched or unbranched, saturated or unsaturated organic radical containing at least two carbon atoms, having at least one amide group and at least one tertiary amino group.

19 Claims, No Drawings

(51) Int. Cl.
*C07C 271/26* (2006.01)
*C09D 7/45* (2018.01)
*C09D 7/65* (2018.01)
*C09D 17/00* (2006.01)

(56) References Cited

U.S. PATENT DOCUMENTS

| | | | |
|---|---|---|---|
| 4,647,647 | A | 3/1987 | Haubennestel et al. |
| 4,777,195 | A | 10/1988 | Hesse et al. |
| 4,795,796 | A | 1/1989 | Haubennestel et al. |
| 4,942,213 | A | 7/1990 | Haubennestel et al. |
| 6,156,814 | A | 12/2000 | Chen et al. |
| RE38,201 | E | 7/2003 | Chen et al. |
| 7,803,395 | B2 | 9/2010 | Datta et al. |
| 8,337,487 | B2 | 12/2012 | Datta et al. |
| 9,447,292 | B2 | 9/2016 | Omeis et al. |
| 9,573,103 | B2 | 2/2017 | Göbelt et al. |
| 2005/0043816 | A1 | 2/2005 | Datta et al. |
| 2011/0014289 | A1 | 1/2011 | Datta et al. |
| 2011/0027585 | A1* | 2/2011 | Pritschins ............ B01F 17/005 428/375 |
| 2013/0316098 | A1* | 11/2013 | Lubnin ............... C08F 283/006 428/32.16 |
| 2014/0012036 | A1 | 1/2014 | Omeis et al. |
| 2014/0194537 | A1 | 7/2014 | Göbelt et al. |

FOREIGN PATENT DOCUMENTS

| | | |
|---|---|---|
| EP | 0 318 999 A2 | 6/1989 |
| EP | 1 038 896 A2 | 9/2000 |
| WO | WO 2012/101180 A1 | 8/2012 |
| WO | WO 2012/175159 A1 | 12/2012 |
| WO | WO-2015079033 A1 * | 6/2015 ......... C08G 73/0206 |

OTHER PUBLICATIONS

Yoon et al. Advanced Institute of Science and Technology, Taejon 305-701, S. KoreaPolymer (Korea) (1999), 23(6), 916-925.*
PCT/EP2016/062719—International Search Report, dated Sep. 7, 2016. English Translation.
PCT/EP2016/062719—International Written Opinion, dated Sep. 7, 2016. English Translation.
PCT/EP2016/062719—International Preliminary Report on Patentability, dated Dec. 5, 2017.
Gross, A., et al., "Synthesis and Copolymerization of Macromonomers Based on 2-Nonyl- and 2-Phenyl-2-Oxazoline", Macromolecular Chemistry and Physics, Sep. 1996, pp. 2811-2826, vol. 197, Issue 9. Abstract only.
Isocyanate: Technical Information ISONATE™ 143L, Dow Chemical Company, Form No. 400-00101503en, Rev: Aug. 3, 2011, pp. 1-4.

* cited by examiner

REACTION PRODUCTS CONTAINING AMIDOAMINE GROUPS

CROSS REFERENCE TO RELATED APPLICATIONS

This application is a national stage application of International Application No. PCT/EP2016/062719, filed 3 Jun. 2016, which claims priority from European Patent Application No. 15170609.0, filed 3 Jun. 2015, which applications are incorporated herein by reference.

The present invention relates to reaction products containing amido amine groups, to a process for preparation thereof, to the use thereof as wetting agents, dispersants and/or dispersion stabilizers, and to compositions comprising them.

Wetting agents in dissolved or dispersed form in a liquid lower the surface tension or interfacial tension and hence increase the wetting capacity of the liquid. In this way, wetting agents in many cases actually enable any surface wetting at all.

Dispersants are generally suitable for stabilization of solid particles in binders, varnishes, pigment pastes, plastics and plastics mixtures, adhesives and sealants, for reduction of the viscosity of corresponding systems and for improving the flow properties. Dispersion stabilizers are used for stabilization of dispersions that have already been produced.

In order to be able to introduce solids into liquid media, high mechanical forces are required. It is customary to use dispersants to lower the dispersion forces and to keep the total energy input into the system needed for deflocculation of the solid particles as low as possible and hence also the dispersion time as short as possible.

Dispersants of this kind are surface-active substances of anionic, cationic and/or uncharged structure. These substances are either applied directly to the solid in a small amount or added to the dispersion medium. A further major factor is that reagglomeration can occur after the dispersion process even after complete deflocculation of the solid agglomerates into primary particles, which partly or completely negates the expenditure on dispersion. Inadequate dispersion or reagglomeration typically results in unwanted effects, such as a rise in viscosity in liquid systems, a drift in the hue and a loss of gloss in varnishes and coatings, and also a reduction in the mechanical strength and material homogeneity in plastics.

Useful wetting agents and dispersants in practice include various types of compound. The particular reason for this is that there exist a high number of different systems based, in particular, on various kinds of binders combined with different particles to be dispersed, such as pigments, fillers and fibers.

WO-A-2012/175159, for example, describes the preparation of specific additive compositions which can be regarded as high-quality wetting agents and dispersants. However, these additive compositions are not considered to be the optimal and s complete solution for many dispersion tasks, especially owing to limited universality with respect to the solids to be dispersed.

It was thus an object of the present invention to provide high-quality products usable with maximum universality that are suitable as wetting agents and/or dispersants and/or dispersion stabilizers.

The object is achieved by provision of reaction products containing amido amine groups, comprising one or more species of the general formula (I):

(I)

where p+y=w and
w is an integer from 1 to 10,
p is an integer from 1 to 10,
y is an integer from 0 to 9, and
X is independently O, NH and/or $NZ^2$ and
XH is independently a hydroxyl group OH, a primary amino group $NH_2$ and/or a secondary amino group $NHZ^2$
where
$Z^2$ is independently a branched or unbranched, saturated or unsaturated organic radical $G(U)_a$ where U is independently a hydroxyl group, a primary amino group or a secondary amino group and
a is an integer from 0 to 9,
where p+y+a≤10, and
G is a branched or unbranched, saturated or unsaturated organic radical, the p $R^1$ radicals are independently a radical of the general formula (II)

(II)

in which the p Y radicals are independently a branched or unbranched, saturated or unsaturated organic radical which has 1 to 1000 carbon atoms and does not contain any hydroxyl groups, any primary amino groups or any secondary amino groups,
the p $R^2$ radicals are independently a branched or unbranched, saturated or unsaturated organic radical having 6 to 20 carbon atoms, and
$Z^1$ is a branched or unbranched, saturated or unsaturated organic radical containing at least two carbon atoms, having at least one amide group and at least one tertiary amino group.

Preferably, the "reaction product containing amido amine groups" comprises one or more species of the general formula (I) as main reaction product(s), meaning that the amount of the species of the reaction product containing amido amine groups covered by the general formula (I) is at least 40% by weight, preferably at least 60% by weight and more preferably at least 90% by weight, based on the total weight of the reaction product containing amido amine groups. Most preferably, the reaction product containing amido amine groups consists essentially of species of the general formula (I). Owing to the merely commercial purity levels of the reactants and/or side reactions that possibly occur in the preparation of the reaction products containing amido amine groups, "essentially consisting of" species of the general formula (I) is understood here to mean a content of species of the formula (I) in the total weight of the reaction product containing amido amine groups of at least 95% by weight.

The term "species" here encompasses both compounds having a specific molecular weight and species that contain polymeric radicals and hence have a number-average and a weight-average molecular weight.

The "reaction products containing amido amine groups" may in the simplest case be molecularly homogeneous products if exclusively molecularly homogeneous, essentially chemically pure compounds Y—O—CO—NH—$R^2$—NCO and $(HX)_p$—$Z^1$—$(HX)_y$ are used for preparation thereof, in which Y is consequently not polymeric, all Y are identical, all $R^2$ are identical, all X are identical and all $Z^1$ are identical.

In the simplest case, however, molecular inhomogeneity of the "reaction products containing amido amine groups" can already be obtained if p+y>1 and if the sum total of p and y is greater than the number of species Y—O—CO—

NH—R²—NCO, even if Y is not polymeric, all Y are identical, all R² are identical, all X are identical and all Z¹ are identical. In this case, molecular distributions are obtained in that the "reaction products containing amido amine groups" include different species of the general formula (I) with different values for p and y values.

However, the "reaction products containing amido amine groups" may also be molecularly inhomogeneous products. This is the case, for example, when the Y radical present in the R¹ radical is polymeric in nature and hence per se introduces molecular inhomogeneity into the products.

Finally, the "reaction products containing amido amine groups" may also be mixtures when the reactants contain, for example, different R¹ and/or Z¹ radicals. The mixtures may be mixtures of chemically homogeneous reaction products containing amido amine groups, mixtures of reaction products containing amido amine groups that contain polymeric radicals, or mixtures of one or more chemically homogeneous reaction products containing amido amine groups with one or more reaction products containing amido amine groups and polymeric radicals.

In the context of this invention, the terms "hydroxyl group" and "primary amino group" and "secondary amino group" should be understood in the sense of their general meaning. This means more particularly that they are present as an independent functional group and not part of an overall further functional group. Thus, in the context of this invention, the OH functionality of a carboxyl group is not a hydroxyl functionality.

The invention also relates to a process for preparing the inventive reaction products containing amido amine groups or the species of the general formula (I) that are present therein.

In the process of the invention for preparing the inventive reaction products containing amido amine groups,
i) at least one diisocyanate R²(NCO)₂ is reacted with at least one monoalcohol Y—OH to form a urethane of the general formula (III)

Y—O—CO—NH—R²—NCO (III)

where
R² and Y are as defined above, and
ii) p urethanes of the general formula (III) are reacted with one or more components that introduce the Z¹—(XH)_y group to give a reaction product containing amido amine groups, comprising one or more species of the general formula (I)

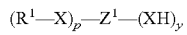
(R¹—X)_p—Z¹—(XH)_y (I).

where p, y, R¹, X and Z¹ are as defined above.
Diisocyanate R²(NCO)₂

In the process of the invention, the inventive reaction products containing amido amine groups are prepared using diisocyanates R²(NCO)₂. Corresponding diisocyanates are known from the prior art. The R² radical corresponding to the diisocyanate R²(NCO)₂ is a branched or unbranched, saturated or unsaturated organic radical having 6 to 20 carbon atoms. The organic R² radical may additionally contain uretdione and/or urethane groups, but ones that do not react under the given conditions. This is the case especially when the reaction mixtures do not contain any primary and/or secondary amino groups. It is therefore preferred that, if R² contains uretdione and/or urethane groups, the X group is represented by oxygen atoms.

Preferably, the organic R² radical is in the form of a hydrocarbyl radical, more preferably of an arylene group, of an alkylarylene group and/or of an acyclic, cyclic, branched or unbranched alkylene group.

Diisocyanates of this kind are, for example, 1,4-diisocyanatobutane, hexamethylene diisocyanate (HDI), 2-methyl-1,5-diisocyanatopentane, 1,5-diisocyanato-2,2-dimethylpentane, 2,2,4- or 2,4,4-trimethyl-1,6-diisocyanatohexane, 1,10-diisocyanatodecane, 1,3- and 1,4-diisocyanatocyclohexane, 1,3- and 1,4-bis(isocyanatomethyl)cyclohexane, 1-isocyanato-3,3,5-trimethyl-5-isocyanatomethylcyclohexane (isophorone diisocyanate, IPDI), 4,4'-diisocyanatodicyclohexylmethane (H12MDI), tolylene diisocyanate (TDI), 1-isocyanato-1-methyl-4(3)isocyanatomethylcyclohexane, diphenylmethane diisocyanate (MDI), bis(isocyanatomethyl)norbornane and 1,3- and 1,4-bis(2-isocyanatoprop-2-yl)benzene (TMXDI) or mixtures of such diisocyanates. The monomeric diisocyanates mentioned may be used as such or in the form of their oligomeric or polymeric diisocyanate-functional derivatives having uretdione and/or urethane groups.

Examples of diisocyanates available as commercial products are Desmodur T100 (100% 2,4-TDI, Bayer AG), Desmodur T80 (80% 2,4-TDI, 20% 2,6-TDI, Bayer AG), Desmodur T65 (65% 2,4-TDI, 35% 2,6-TDI, Bayer AG), Desmodur N3400 (aliphatic HDI uretdione, Bayer AG), Thanecure T9 (aromatic TDI uretdione, TSE Industries), Crelan VP LS 2147 and Crelan VP LS 2347 (aliphatic IDPI uretdiones, Bayer AG). Preparation of the inventive reaction products containing amido amine groups can be accomplished using one or more monomeric, oligomeric or polymeric diisocyanates.

Selectivity with regard to the preparation of the urethane covered by the general formula (III) which is produced in step i) is increased in the process of the invention preferably by using a diisocyanate R²(NCO)₂ having two isocyanate groups of different reactivity. More preferably, the diisocyanate R²(NCO)₂ having two isocyanate groups of different reactivity is selected from the group consisting of toluene 2,4-diisocyanate and isophorone diisocyanate.

In the preparation of the urethane of the general formula (III) in step i), the diisocyanate R²(NCO)₂ is used at least in an equimolar ratio to the monoalcohol Y—OH. Preferably, the diisocyanate R²(NCO)₂ is used in step i) in a molar excess, as a result of which a higher selectivity is achieved in that preferably only exactly one NCO group of the diisocyanate is converted in step i).

The greater the molar excess of the diisocyanate, the higher the selectivity normally is with respect to the preparation of the urethane covered by the general formula (III) which is produced in step i). The unconverted diisocyanate that remains owing to use in excess is preferably at least partly (but very substantially completely) removed from the reaction mixture, preferably by distillation, in order ultimately to keep the proportion of by-products formed therefrom at a low level. Preferably at least 75 mol %, more preferably at least 90 mol % and most preferably the entire fraction of the unconverted portion of the diisocyanate R²(NCO)₂ is removed from the reaction mixture. The diisocyanate worsens the quality of the process product and is considered to be environmentally harmful.

Preferably, in step i), the diisocyanate R²(NCO)₂ is used relative to the monoalcohol Y—OH in a molar ratio of at least 1.1:1.0, more preferably of at least 2.0:1.0 and most preferably of at least 2.5:1.0.

It is most preferred that, in step i), both one or more diisocyanates having isocyanate groups of different reactivity are used and a molar excess of isocyanate component in relation to the monoalcohol Y—OH is used.

It should be emphasized that the inventive reaction products containing amido amine groups that are preparable by the process of the invention or the species of the general formula (I) that are present therein exhibit good dispersing action with regard to a broad spectrum of solids to be dispersed. One way in which this is manifested is that solids having acidic, neutral and basic surfaces can each be effectively dispersed.

The reaction products containing amido amine groups that are preparable by the process of the invention or the species of the general formula (I) that are present therein are of particularly high quality and universally usable as wetting agents and s dispersants. In specific terms, it can be stated that the reaction products containing amido amine groups that are preparable in accordance with the invention or the species of the general formula (I) that are present therein can be used successfully both in polar and in nonpolar binder systems, and at the same time exhibit excellent compatibility as wetting agents and dispersants or as dispersion stabilizers. This ensures successful use in combination with a wide variety of different binders and coating materials. In addition, the reaction products containing amido amine groups that are preparable by the process of the invention or the species of the general formula (I) that are present therein enable flocculation-free miscibility of pastes, especially pigment pastes, or of the binders produced with these pastes.

Furthermore, the inventive reaction products containing amido amine groups or the species of the general formula (I) that are present therein are suitable as dispersion stabilizers, especially also as emulsion stabilizers. The use of the reaction products containing amido amine groups that are preparable by the process of the invention or the species of the general formula (I) that are present therein distinctly reduces the viscosity of the millbase introduced during the dispersion and, in this way, enables the production of formulations having a high solids content. In this way, for better environmental compatibility, the proportion of (volatile) solvents can be reduced. In summary, it can be stated that the reaction products containing amido amine groups that are preparable by the process of the invention or the species of the general formula (I) that are present therein, with good stabilization of pigments or fillers, lower the millbase viscosity of corresponding varnishes, pastes or plastics formulations to such an extent that processing is possible at a high fill level without any adverse effect on the stability of the cured varnishes. Finally, it should be mentioned that the process of the invention is performable in a comparatively simple and economically viable manner, and the starting materials used are generally readily available.

Monohydroxy-functional Alcohol Y—OH

The alcohol Y—OH used in the process of the invention may have additional heteroatoms such as O, S, Si and/or N, or contain ether, urethane, carbonate, amide, urea and/or ester groups. However, the hydroxyl groups, primary amino groups and secondary amino groups that are extremely reactive toward isocyanate groups must s not be present in Y. Optionally, in the Y groups, hydrogen may be replaced by halogen (for example fluorine and/or chlorine). The Y radical may bear further groups, such as C=C double bonds, which are inert in the formation of the addition product. Any ester, ether, urethane, carbonate and/or siloxane groups present may be present in block structure (for example poly(ethylene oxide block-propylene oxide block-epsilon-caprolactone), form a gradient or else be in a random arrangement.

Y as Ether Radical or Polyether Radical:

It is also possible to use monohydroxy polyethers as Y—OH. These can be obtained, for example, by alkoxylation of a monohydroxy-functional starter component T-OH. In principle, all Y—OH components described are useful as starter component T-OH. For preparation, for example, alkanols, cycloalkanols or phenols can be reacted with alkylene oxides such as ethylene oxide, propylene oxide, butylene oxide, styrene oxide, aliphatic or aromatic glycidyl ethers such as isopropyl glycidyl ether, butyl glycidyl ether, allyl glycidyl ether, 2-ethylhexyl glycidyl ether, cresyl glycidyl ether and phenyl glycidyl ether. It is also possible to use mixtures of these raw materials. In the case of mixed polyethers, these may be arranged randomly, in gradient form or in blocks.

These polyethers frequently have a number-average molecular weight ($M_n$) in the range from about 100 to 25 000, particularly frequently from 150 to 15 000 and particularly typically from 200 to 10 000 g/mol.

Preference is given to polyethers based on ethylene oxide, propylene oxide and mixtures thereof.

Examples are hydroxy-functional vinyl compounds, such as hydroxybutyl vinyl ether, monohydroxy-functional polyoxyalkylene monoalcohols, such as allyl polyethers (e.g. Polyglycol A 350, Polyglycol A 500, Polyglycol A 1100, Polyglycol A 11-4, Polyglycol A 20-10 or Polyglycol A 20-20 from Clariant AG or Pluriol® A 010 R, Pluriol® A 11 RE, Pluriol® A 13 R, Pluriol® A 22 R or Pluriol® A 23 R from BASF AG), vinyl polyethers (such as Polyglycol V 500, Polyglycol V 1100 or Polyglycol V 5500 from Clariant AG), methanol-started polyoxyethylene monoalcohols (such as Pluriol" A 350 E, Pluriol® A 500 E, Pluriol® A 750 E, Pluriol® A 1020 E, Pluriol® A 2000 E or Pluriol A 5010 E from BASF AG), alkanol-started polyoxypropylene monoalcohols (for example Polyglycol B01/20, Polyglycol B01/40, Polyglycol B01/80, Polyglycol B01/120 or Polyglycol B01/240 from Clariant AG or Pluriol® A 1350 P or Pluriol® A 2000 P from BASF AG) and polyalkoxylates that have been started with various fatty alcohols and io have a variable degree of alkoxylation (known under the Lutensol® A, Lutensol® AT, Lutensol® AO, Lutensol® TO, Lutensol® XP, Lutensol® XL, Lutensol® AP and Lutensol® ON trade names from BASF SE). Preference is given to using polyoxyalkylene monoalcohols containing ethylene oxide and/or propylene oxide and/or butylene oxide groups and optionally modified with styrene oxide, phenyl glycidyl ether or cresyl glycidyl ether. Particular preference is given to the use of polyoxyalkylene monoalcohols (such as Polyglycol B 11/50, Polyglycol B 11/70, Polyglycol B 11/100, Polyglycol B 11/150, Polyglycol B 11/300 or Polyglycol B 11/700 from Clariant AG, Pluriol® A 1000 PE, Pluriol® A 1320 PE, or Pluriol® A 2000 PE from BASF AG or Terralox WA 110 from DOW Chemicals), which are butanol-started polyoxyalkylenes formed from ethylene oxide and propylene oxide with a terminal OH group.

In general, Y contains 1 to 450 ether oxygen atoms which are preferably present in groups having ether oxygen atoms that are derived from polytetrahydrofuran, polyoxetanes and/or polyoxiranes.

Preferably, Y contains 3 to 400 ether oxygen atoms, where at least 50 mol %, preferably at least 80 mol %, of the ether oxygen atoms are present in ethylene oxide and/or polypropylene oxide structural units.

Y as Hydrocarbyl Radical:

The hydrocarbyl radicals are preferably in the form of an aryl radical, of a branched or unbranched aralkyl radical and/or of an acyclic, cyclic branched or unbranched alkyl radical. It is also possible to use mixtures of such compounds, i.e. at least two different compounds Y—OH. The aliphatic or araliphatic compounds Y—OH may be in straight-chain or branched, saturated or unsaturated form. Saturated species are preferred.

Examples of Y—OH with hydrocarbyl radicals are methanol, ethanol, butanol, ethylhexanol, decanol, isotridecyl alcohol, lauryl alcohol, stearyl alcohol, isobornyl alcohol, benzyl alcohol, propargyl alcohol, oleyl alcohol, linoleyl alcohol, oxo alcohols, neopentyl alcohol, cyclohexanol, fatty alcohols, alkylphenols, alkylnaphthols, phenylethanol.

In addition, Y—OH may be polyolefin monools, such as nonhydrogenated, partly hydrogenated and/or fully hydrogenated polybutadienes, non-hydrogenated, partly hydrogenated and/or fully hydrogenated polyisoprenes, polyisobutylenes, polypropylenes or ethylene/butylene copolymers. These compounds are known. For example, the route to hydroxy-functional polyisobutylenes is described in U.S. Pat. No. 6,875,897.

Y as Ester Radical or Polyester Radical:

As Y—OH it is also possible to use monohydroxy monoesters and monohydroxy polyesters.

Hydroxy-functional acrylates or methacrylates, such as hydroxyethyl acrylate, hydroxyethyl methacrylate, hydroxybutyl (meth)acrylate, are examples of suitable monohydroxy monoesters.

Polyesters can be prepared, for example, by reaction of dicarboxylic acids and the esterifiable derivatives thereof, such as anhydrides, acid chlorides or dialkyl esters (such as dimethyl esters or diethyl esters) by reaction with diols and monofunctional starter components. The formation of dihydroxy polyesters can be suppressed if required through use of appropriately stoichiometric amounts of monohydroxy compounds. The esterification can be conducted in neat form or else by azeotropic esterification in the presence of an entraining agent. Examples of dicarboxylic acids are succinic acid, maleic acid, fumaric acid, glutaric acid, adipic acid, sebacic acid, pimelic acid, phthalic acid or dimerized fatty acids, and the isomers and hydrogenation products thereof. Examples of corresponding diols are: ethylene glycol, propane-1,2-diol, propane-1,3-diol, butane-1,4-diol, hexane-1,6-diol, neopentyl glycol, cis-1,2-cyclohexanedimethanol, trans-1,2-cyclohexanedimethanol, and polyglycols based on ethylene glycol and/or propylene glycol.

Preferred polyesters for use as Y—OH are those which can be obtained by polycondensation of one or more optionally alkyl-substituted hydroxycarboxylic acids and/or ring-opening polymerization of the corresponding lactones such as propiolactone, valerolactone, butyrolactone, caprolactone and/or substituted lactones by means of a monohydroxy starter component (as described in U.S. Pat. No. 4,647,647). Preferably, these have a number-average molecular weight $M_n$ of 150 to 5000 g/mol. Usable starter components T-OH are in principle all other compounds listed as Y—OH. It is also possible in each case to use mixtures of the aforementioned compounds. Lactone polymerization is conducted by known processes, initiated, for example, by titanates, p-toluenesulfonic acid or dibutyltin dilaurate, at temperatures of, for instance, 70° C. to 180° C. Particular preference is given to polyesters based on ε-caprolactone, optionally in combination with δ-valerolactone.

Y as Urethane Radical or Polyurethane Radical:

As Y—OH it is also possible to use polyurethanes, polyether-polyurethanes, polyester-polyurethanes and/or polyether-polyester-polyurethanes, which can be obtained by addition reaction of diisocyanates with dihydroxyl compounds in the presence of monofunctional starter components. Hydroxyl compounds used to form the compounds Y—OH containing urethane groups are preferably diols having 2 to 12 carbon atoms, polyoxyalkylene glycols and dihydroxy-functional polyesters.

Y as Polycarbonate Radical:

The Y radical may also contain carbonate groups as obtained by known reactions with open-chain and/or cyclic carbonates. Suitable examples are linear polyesters or polycarbonatediols that have been modified with carbonates, as used in polyurethane production. Examples are described in U.S. Pat. No. 4,101,529. Suitable carbonates are, for example, aliphatic, cycloaliphatic, araliphatic and/or aromatic carbonic esters, such as dialkyl carbonates, e.g. dimethyl carbonate, diethyl carbonate or diphenyl carbonate, catechol carbonate or cyclic alkylene carbonates. Particularly suitable are cyclic alkylene carbonates having 5- or 6-membered rings, which may optionally be substituted. Preferred substituents are aliphatic, cycloaliphatic and/or aromatic groups having up to 30 carbon atoms. Examples of suitable cyclic alkylene carbonates are ethylene carbonate, propylene carbonate, glycerol carbonate, trimethylene carbonate, 4-methyltrimethylene carbonate, 5-methyltrimethylene carbonate, 5,5-dimethyltrimethylene carbonate, 5,5-diethyltrimethylene carbonate or 5-methyl-5-propyltrimethylene carbonate.

Y as Polyoxazoline Radical:

It is also possible for monohydroxy-functional poly-2-alkyl-2-oxazolines or poly-2-alkyl-2-oxazines to function as Y—OH. Poly-2-alkyl-2-oxazolines or poly-2-alkyl-2-oxazines are obtained by cationic, ring-opening polymerization of 2-alkyl-2-oxazolines or 2-alkyl-2-oxazines with initiators such as para-toluenesulfonic acid, methyl tosylate or methyl triflate. The oxazolinium or oxazinium end groups that result from the living cationic polymerization mechanism can be converted to the more stable hydroxy amides by alkaline hydrolysis via amino ester end groups. An alternative route for preparation of monohydroxy-functional poly-2-alkyl-2-oxazolines or poly-2-alkyl-2-oxazines is polymerization with 2-(4-hydroxyphenyl)-N-methyl-2-oxazolinium trifluoromethanesulfonate as the initiating species (A. Gross, G. Maier, O. Nuyken, Macromol. Chem. Phys. 197, 2811-2826 (1996)). Through choice of the alkyl substituent, it is possible to control the compatibility; for example, poly-2-ethyl-2-oxazoline is suitable for highly polar systems by virtue of its water solubility, while poly-2-lauryl-2-oxazoline, for example, is compatible in nonpolar systems. If block copolymers are formed from 2-ethyl-2-oxazoline and 2-lauryl-2-oxazoline, the polymers feature particularly broad compatibility. Poly-2-alkyl-2-oxazolines or poly-2-alkyl-2-oxazines of this kind usually have a number-average molecular weight $M_n$ of 300 to 20 000 g/mol, preferably of 500 to 10 000 g/mol. Among other compounds, it is possible to use various different 2-oxazolines which may possibly have additional functional groups. Species of this kind are, for example, corresponding fatty acid-based 2-oxazolines.

Y as OH-functional Polymer of Ethylenically Unsaturated Compounds:

As Y—OH it is also possible to use OH-functional polymers of ethylenically unsaturated monomers. The OH functions can be introduced in a known manner via monohydroxy-functional ethylenically unsaturated monomers, via monohydroxy-functional initiators or via monohydroxy-functional chain transfer agents, for example in free-radical polymerization. Particularly high selectivities in relation to the monohydroxy functionality can be achieved by controlled or living polymerization methods, for example ATRP, NMP, RAFT or anionic polymerization. Preference is given to monohydroxy-functional polyacrylic esters or polymethacrylic esters. Compounds of this kind have already been used in this field of industry for preparation of other dispersants, as described in U.S. Pat. No. 4,032,698 or in EP 318 999. For example, monohydroxy-functional polyacrylate macromers such as Actflow UMM 1001 from Soken Chemical & Engineering Co. are commercially available. These polyacrylates usually have a number-average molecular weight Mn of 300 to 20 000 g/mol, preferably usually from 500 to 10 000 g/mol. These may be arranged in a block structure or else randomly or form a gradient.

Examples of OH-functional ethylenically unsaturated monomers are hydroxyalkyl (meth)acrylates of straight-chain, branched or cycloaliphatic diols having
2 to 36 carbon atoms, such as
3-hydroxypropyl methacrylate, 3,4-dihydroxybutyl monomethacrylate, 2-hydroxyethyl (meth)acrylate, 4-hydroxybutyl (meth)acrylate,
2-hydroxypropyl methacrylate, 2,5-dimethylhexane-1,6-diol monomethacrylate; caprolactone- and/or valerolactone-modified hydroxyalkyl (meth)acrylates (where the hydroxy (meth)acrylates are preferably derived from straight-chain, branched or cycloaliphatic diols having 2 to 8 carbon atoms);
OH-functional poly(ethylene glycol)(meth)acrylate and OH-functional poly(propylene glycol)(meth)acrylate.

Examples of further ethylenically unsaturated monomers are alkyl (meth)acrylates of straight-chain, branched or cycloaliphatic alcohols having 1 to 22 carbon atoms, such as methyl (meth)acrylate, ethyl (meth)acrylate, n-butyl (meth)acrylate, i-butyl (meth)acrylate, t-butyl (meth)acrylate, lauryl (meth)acrylate, 2-ethylhexyl (meth)acrylate, stearyl (meth)acrylate, cyclohexyl (meth)acrylate, isobornyl (meth)acrylate and t-butyl (meth)acrylate; aralkyl (meth)acrylates such as benzyl methacrylate and aryl (meth)acrylates such as phenyl acrylate (where the aryl radicals may each be unsubstituted or up to tetrasubstituted), such as
4-nitrophenyl methacrylate;
mono(meth)acrylates of ethers, polyethylene glycols, polypropylene glycols or mixed polyethylene/propylene glycols having 5 to 80 carbon atoms, such as tetrahydrofurfuryl methacrylate, methoxyethoxyethyl methacrylate,
1-butoxypropyl methacrylate, cyclohexyloxymethyl methacrylate, methoxymethoxyethyl methacrylate, benzyloxymethyl methacrylate, furfuryl methacrylate, 2-butoxyethyl methacrylate, 2-ethoxyethyl methacrylate, allyloxymethyl methacrylate,
1-ethoxybutyl methacrylate, 1-ethoxyethyl methacrylate, ethoxymethyl methacrylate, poly(ethylene glycol) methyl ether (meth)acrylate, poly(propylene glycol) methyl ether (meth)acrylate; tertiary aminoalkyl (meth)acrylates, such as N,N-dimethylaminoethyl (meth)acrylate,
2-trimethylammonioethyl methacrylate chloride and N,N-dimethylaminopropyl (meth)acrylate; (meth)acrylates of halogenated alcohols, such as perfluoroalkyl (meth)acrylates having 6 to 20 carbon atoms; styrene and substituted styrenes, such as 4-methylstyrene, methacrylonitrile and acrylonitrile; ethylenically unsaturated heterocycles, for example 4-vinylpyridine and 1-[2-(methacryloyloxy)ethyl]-2-imidazolidinone;
vinyl esters of carboxylic acids having 1 to 20 carbon atoms, such as vinyl acetate;
maleimide, N-phenylmaleimide and N-substituted maleimides with straight-chain, branched or cycloaliphatic alkyl groups having 1 to 22 carbon atoms, such as N-ethylmaleimide and N-octylmaleimide; (meth)acrylamide;

N-alkyl- and N,N-dialkyl-substituted acrylamides having straight-chain, branched or cycloaliphatic alkyl groups having 1 to 22 carbon atoms, such as N-(t-butyl)acrylamide and N,N-dimethylacrylamide.

Preferred non-OH-functional monomers are alkyl (meth)acrylates, aryl (meth)acrylates, aralkyl (meth)acrylates and styrene.

Y as Polysiloxane Radical:

As Y—OH it is also possible to use monohydroxy-functional polysiloxanes. The polysiloxanes can preferably be described by the following general formula:

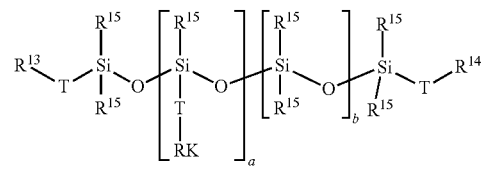

with
T=$C_1$-$C_{14}$-alkylene,
RK=unbranched polyether radical formed from alkylene oxide units having 1-6 carbon atoms, and/or aliphatic and/or cycloaliphatic and/or aromatic polyester radical having a weight-average molecular weight between 200 and 4000 g/mol,
$R^{13}$ and $R^{14}$ are each independently represented by $C_1$-$C_{14}$-alkyl, -aryl or -aralkyl, —O($C_1$-$C_{14}$-alkyl, -aryl or -aralkyl), —OCO($C_1$-$C_{14}$-alkyl, -aryl or -aralkyl), —O—CO—O($C_1$-$C_{14}$-alkyl, -aryl or -aralkyl), —OSO$_2$($C_1$-$C_{14}$-alkyl, -aryl or -aralkyl), —H, —Cl, —F, —OH, —R, —RK,
$R^{15}$=$C_1$-$C_{14}$-alkyl, -aryl or -aralkyl,
a=0-20, preferably 1-15, more preferably 1-8,
b=2-300, preferably 10-200, more preferably 15-100 and
The polysiloxane radicals may also take the form of organomodified polysiloxane radicals.

Preparation of Urethanes of the General Formula (III) from Y—OH and $R^2(NCO)_2$ The urethanes of the general formula (III) are also referred to hereinafter, especially in the examples, as monoadducts M.

In the process of the invention, the isocyanate addition, according to the reactivity of the individual coreactants, can be effected within the temperature range which is customary for this kind of reaction from room temperature to about 150° C., preferably to 100° C., more preferably to 70° C. For acceleration and to reduce the level of side reactions, it is possible to use the known and customary catalysts, such as tertiary amines, triethylamine, dimethylcyclohexylamine, N-methylmorpholine, N,N'-dimethylpiperazine, 2-(dimethylaminoethoxy)ethanol, diazabicyclo[2.2.2]octane and the like, and also especially organic metal compounds, such as titanic esters, iron compounds such as iron(III) acetylacetonate, tin compounds, for example tin diacetate, tin dioctoate, tin dilaurate or the dialkyl derivatives of tin dialkyl salts of aliphatic carboxylic acids such as dibutyltin diacetate, dibutyltin dilaurate or the like. These catalysts are typically used in amounts of 0.0001 to 0.1 part by weight per 100 parts by weight of diisocyanate.

Reaction Product Containing Amido Amine Groups $(R^1—X)_p—Z^1—(XH)_y$

The reaction product of the invention containing amido amine groups, comprises one or more species of the general formula (I):

where p+y=w, and
w is an integer from 1 to 10,
p is an integer from 1 to 10 and
y is an integer from 0 to 9.

X is independently O, NH and/or $NZ^2$ and the XH group is independently a hydroxyl group OH, a primary amino group NI-I2 and/or a secondary $NHZ^2$. More preferably, X is O and the XH group is a hydroxyl group OH.

$Z^2$ is independently a branched or unbranched, saturated or unsaturated organic radical $G(U)_a$ where U is independently a hydroxyl group, a primary amino group or a secondary amino group and
a is an integer from 0 to 9,
where p+y+a≤10.

The G group is a branched or unbranched, saturated or unsaturated organic radical, said radical containing preferably 1 to 30 carbon atoms, more preferably 1 to 18 carbon atoms and especially preferably 1 to 10 carbon atoms.

The organic G radical does not have any HX groups reactive toward isocyanate groups. However, the organic G radical may optionally also contain heteroatoms, especially oxygen and/or nitrogen atoms. These are preferably in the form of ether oxygen atoms and/or tertiary amino groups.

The restriction of the sum total of p+y+a to not more than 10 takes account of the fact that the possible organic $Z^2$ radical(s) can have HX groups that are also reactive toward isocyanate groups. However, it is essential to the invention that a species of the general formula (I) contains not more than a sufficient number of HX groups that the sum total of all y+a HX groups and all p $R^1$—X radicals does not exceed a maximum number of 10.

The $Z^1$ group present in the above formula (I) can generally be referred to as head group. This head group $Z^1$ represents a branched or unbranched, saturated or unsaturated organic radical containing at least two carbon atoms, having at least one amide group and at least one tertiary amino group. Preferably, the head group $Z^1$ contains 2 to 50 carbon atoms, more preferably 2 to 30 carbon atoms and more preferably 2 to 20 carbon atoms.

Component $(HX)_p$—$Z^1$—$(HX)_y$

The species which is free of urethane groups, is reactive toward isocyanate groups and corresponds to the formula (I) is of the general formula (IV)

$$(HX)_p\text{—}Z^1\text{—}(HX)_y \quad (IV)$$

where p, y, X and $Z^1$ are as defined for the general formula (I). Species of the general formula (IV) are generally not commercially available. They are preferably obtained by reacting one or more components A with one or more components B and/or C.

The species of the general formula (IV) are also referred to hereinafter, especially in the examples, as amido amines AA.

Component A is independently selected from the group of ethylenically unsaturated carboxylic acids, esters thereof and acid halides thereof, where at least one C=C double bond and at least one C=O double bond are in conjugated form and the C=O double bond is selected from the group of the carboxylic acids, the carboxylic esters and the carbonyl halides.

Preference is given to using ethylenically unsaturated carboxylic esters as component A.

Examples of ethylenically unsaturated ester compounds in which the C=C and the C=O double bond of the ester group are conjugated are alkyl acrylates, for example methyl acrylate, ethyl acrylate, n-propyl acrylate, i-propyl acrylate, n-butyl acrylate, i-butyl acrylate, t-butyl acrylate, 2-ethyl-hexyl acrylate, cyclohexyl acrylate and lauryl acrylate; monoacrylates of short-chain ethers, such as tetrahydrofurfuryl acrylate, methoxyethoxyethyl acrylate, 1-butoxypropyl acrylate, cyclohexyloxymethyl acrylate, methoxymethoxyethyl acrylate, benzyloxymethyl acrylate, furfuryl acrylate, 2-butoxyethyl acrylate, 2-ethoxyethyl acrylate, allyloxymethyl acrylate, 1-ethoxybutyl acrylate, 1-ethoxyethyl acrylate, ethoxymethyl acrylate; maleic diesters, such as dimethyl maleate, diethyl maleate and dibutyl maleate; fumaric diesters, such as dimethyl fumarate, diethyl fumarate and dibutyl fumarate; itaconic esters, such as dimethyl itaconate and diethyl itaconate.

Preferably, component A is selected from the acrylic esters, more preferably from the s short-chain alkyl acrylates having a $C_1$- to $C_6$-alkyl chain. Most preferred are methyl acrylate and ethyl acrylate.

Component B is of the general formula (V)

$$(R^3)_x\text{—HN—}(R^4)_z \quad (V)$$

where x+z=2 and
x is an integer from 0 to 2,
z is an integer from 0 to 2, and
$R^3$ is independently H or a branched or unbranched, saturated or unsaturated organic radical having 1 to 12 carbon atoms, and
$R^4$ is independently a branched or unbranched, saturated or unsaturated organic radical having 2 to 12 carbon atoms and 1 to 3 tertiary amino groups, which may optionally also have 1 to 3 primary and/or secondary amino groups.

If two or more components B are present, these are independently represented by the above formula.

Examples of component B in which x assumes the value of 2 are butylamine, hexylamine, dibutylamine, diethylamine, dipropylamine, benzylamine, N-benzylmethylamine and N-phenylbenzylamine.

Examples of component B in which x assumes the value of 1 are N,N-dimethylaminoethylamine, N,N-dimethylaminopropylamine, N,N-diethylaminoethylamine, N,N-diethylaminopropylamine, tris[2-(methylamino)ethyl]amine, N,N-dimethyldipropylenetriamine, N,N-bis(3-aminopropyl)methylamine, tris(3-aminopropyl)amine, tris(2-aminoethyl)amine, 2-(2-methylaminoethyl)pyridine, 2-aminomethylpyridine, 4-aminomethylpyridine, 1-(3-aminopropyl)imidazole and N,N,N'-trimethylenediamine.

One example of component B in which x assumes the value of 0 is bis(3-dimethylaminopropyl)amine.

Component C is of the general formula (VI)

$$(R^5)_k\text{—HN—}(R^6)_n \quad (VI),$$

where k+n=2 and
k is an integer from 0 to 1,
n is an integer from 1 to 2, and
$R^5$ is H or a branched or unbranched, saturated or unsaturated organic radical having 1 to 12 carbon atoms, and
$R^6$ is independently a branched or unbranched, saturated or unsaturated organic radical having 2 to 12 carbon atoms and 1 to 4 hydroxyl groups, which may optionally contain a tertiary amino group.

If two or more components C are present, these are independently represented by the above formula.

Examples of component C in which k assumes the value of 0 are diethanolamine, diisopropanolamine, dipropanolamine, N-(2'-hydroxyethyl)piperazine, 3-((2-hydroxyethyl)amino)-1-propanol.

Examples of component C in which k assumes the value of 1 are ethanolamine, propanolamine, 4-amino-1-butanol, 3-amino-1-butanol, 1-aminopropan-2-ol, 5-amino-1-pentanol, N-(2-hydroxyethyl)-N-methylpropylene-1,3-diamine, 2-amino-2-ethylpropane-1,3-diol, N-methylethanolamine, N-ethylethanolamine, N-butylethanolamine, N-(2-hydroxyethyl)aniline, 1,1,1-tris(hydroxymethyl)methanamine, aminopropyldiethanolamine, glucosamine and 2-(2-aminoethoxy)ethanol.

Preferably, the species of the general formula (IV) are prepared in two steps.

The first step here is the addition of a primary or secondary amino group of a component B and/or C onto the C=C double bond of a component A in a Michael addition reaction. The corresponding product is a Michael addition product and is referred to hereinafter as intermediate I. These reactions are preferably effected within a temperature range from 0 to 100° C., more preferably from 10 to 80° C. and especially preferably from 15 to 50° C.

Primary amino groups are capable of reacting twice in a Michael addition. For this purpose, the primary amino group of a component B or C first adds on to the C=C double bond of a component A to form a secondary amino group. This secondary amino group is capable of reacting in a further Michael addition with a C=C double bond of a component A to form a tertiary amino group. The double Michael addition product of a component B or C with two independently selected components A is also an intermediate I as described above.

In the second reaction step, at least one of the C=O double bonds present in the intermediate I, selected from the group of a carboxylic acids, carboxylic esters and the carbonyl halides, is reacted with a primary or secondary amino group of a component B or C in an amidation reaction to form a species of general formula (IV). It is preferable that the C=O double bond present in the intermediate is in the form of a carboxylic ester group.

These reactions are preferably effected within a temperature range from 50 to 180° C., more preferably from 70 to 160° C. and especially preferably from 80 to 150° C.

When the intermediate I has more than one C=O double bond selected from the group of the carboxylic acids, the carboxylic esters and the carbonyl halides, these can also be reacted in an amidation reaction with a primary or secondary amino group to give an amide group.

The cleavage products formed in the amidation reaction, for example alcohol formed in the case of the preferred carboxylic ester hydrolysis, are removed from the reaction mixture during or after the reaction. In addition, any solvent used in the s reaction is removed from the reaction mixture.

For example, it is also possible that preparation of a species of the general formula (IV) is accomplished using reactants that are already an intermediate I, such that these can be reacted in one or more amidation reactions with one or more primary or io secondary amino groups of components B and/or C to give products of the general formula (IV).

It is also possible, for example, that preparation of a species of the general formula (IV) is accomplished using reactants having at least one amide group and at least one C=C double bond in conjugation with the C=O double bond of the amide group. Species of the general formula (IV) are then prepared by Michael addition of a primary or secondary amino group of component B or C onto the C=C double bond.

The selection of component B of formula (V) and/or C of the general formula (VI) for preparation of a species of general formula (IV) is not subject to any further restriction and is merely subject to the provision that the resulting product is a species of general formula (IV). This means that the product contains 1 to 10 groups reactive toward isocyanate groups, and also at least one tertiary amino group and at least one amide group.

Process Step ii) of the Process of the Invention

Step ii) of the process of the invention can be conducted either in one stage ii-a) or in a stage sequence ii-b).

When process step ii) of the process of the invention is conducted in one stage ii-a), p urethanes of the general formula (III) are reacted with a species of the general formula (IV) which is free of urethane groups and reactive toward isocyanate groups to give a reaction product containing amido amine groups, comprising one or more species of the general formula (I).

The isocyanate addition can preferably, according to the reactivity of the individual coreactants, be effected within the temperature range which is customary for this kind of reaction from room temperature to about 150° C., preferably to 100° C., more preferably to 70° C.

In the stage sequence ii-b), p urethanes of the general formula (III) are first reacted with an intermediate I to form an intermediate J. As described above, the intermediate I is preferably a Michael addition product of at least one component A with a component B or C. For performance of the stage sequence ii-b), it is essential to the invention that the intermediate I has at least one HX group reactive toward isocyanate groups, with X as defined for the general formula (I). The intermediate J is formed by reaction of an isocyanate group of at least one urethane of the general formula (III) with at least one HX group of the intermediate I. The intermediate J thus formed contains at least one C=O double bond selected from the group of the carboxylic acids, the carboxylic esters and the carbonyl halides, preference being given to carboxylic esters.

Through one or more appropriate amidation reactions with one or more components B and/or C, alongside the formation of the head group $Z^1$, there is simultaneous formation of a reaction product containing amido amine groups, comprising one or more species of general formula (I). These reactions are preferably effected within a temperature range from 50 to 180° C., more preferably from 70 to 160° C. and especially preferably from 80 to 150° C.

The conversion of the isocyanate group(s) of the urethane of the general formula (III) that proceeds in step ii) should be very substantially complete. In an optimal manner, the reaction products containing amido amine groups that are prepared are substantially free of isocyanate groups, especially substantially free of the diisocyanate used in step i).

The reaction products containing amido amine groups that are prepared by the process of the invention—without aftertreatment or purification—typically contain small amounts of diurethane and diurea which arise from side reactions. Possible side reactions are the double reaction of a diisocyanate $R^2(NCO)_2$ with a s monoalcohol Y—OH to form a diurethane of the general formula Y—O—CO—NH—$R^2$—NH—CO—O—Y, and the double reaction of a diisocyanate $R^2(NCO)_2$ with a species of the general formula (IV) to form one or more species of the general formula $(HX)_{y+(p-1)}$—$Z^1$—(X—CO—NH—$R^2$—NH—CO—X)—$Z^1$—$(XH)_{y+(p-1)}$. According to the definition of the X group, the latter reaction gives rise to diurethanes when X=O, to diureas when X=NH or $NZ^2$, and to ureaurethanes if X is different than O and NH/$NZ^2$. Correspondingly small amounts of these by-products do not cause any detriment at all with regard to use as wetting agents and dispersants, and are a clear pointer that the reaction products containing amido amine groups have been prepared using monohydroxy compounds by the process of the invention. In addition, the inventive reaction products containing amido amine groups may also contain a small amount of the unconverted urethane of the formula (III). The use of appropriate amounts of a species of the general formula (IV) in step ii-a) or of the intermediate I in step ii-b) of the process of the invention allows the proportion of the urethane of the general formula (III) to be reduced generally at least almost to zero, which is usually advantageous for the quality of the inventive reaction products containing amido amine groups. Corresponding reactions in step ii) of the process of the invention are preferably considered to have ended when an NCO content of <0.1% is found. The inventive reaction products containing amido amine groups are environmentally friendly, have good storability and—in a corresponding manner to the inventive species of the general formula (I) as such—exhibit excellent properties as wetting agents and dispersants.

Solvent

According to viscosity, the process of the invention can be conducted in neat form or in the presence of suitable solvents, solvent mixtures or other suitable carrier media. Suitable solvents or carrier media are all those that are unreactive or whose reactivity toward the coreactants under the reaction conditions chosen is negligible and in which the reactants and the reaction products are at least partly soluble. Examples of these include hydrocarbons such as toluene, xylene, aliphatic and/or cycloaliphatic petroleum fractions, chlorinated hydrocarbons such as chloroform, trichloroethane, cyclic and acyclic ethers such as dioxane, tetrahydrofuran, polyalkylene glycol dialkyl ethers such as dipropylene glycol dimethyl ether, esters of mono-, di- or s polycarboxylic acids such as ethyl acetate, butyl acetate, butyrolactone, dimethyl 2-methylglutarate, triacetin, phthalates or other plasticizers, di- or polycarboxylic esters, dialkyl esters of $C_2$-$C_4$ dicarboxylic acids that are referred to as "dibasic esters", alkyl glycol esters such as ethyl glycol acetate, methoxypropyl acetate, ketones such as methyl isobutyl ketone, cyclohexanone, acetone, acid amides such as dimethylformamide, N-methylpyrrolidone and the like.

For the performance of the above-described reactions, the solvents should appropriately be selected such that they are inert with respect to the reactants under the reaction conditions.

Appropriately, the solvent(s) or carrier media are selected already taking account of the planned field of use. For example, for use in water-thinnable varnish systems or for coating of pigments in aqueous suspension after the pigment synthesis, preference is given to using solvents that are fully or partly water-thinnable. If the process product is to be used, for example, at a location where the presence of volatile organic compounds (VOCs) is undesirable, the formulation should be in very substantially solvent-free form or in carrier materials that are correspondingly regarded as being VOC-free.

According to the field of use, the solvents used for the synthesis may remain in the reaction mixture or are wholly or partly removed and optionally replaced by other solvents or carrier media.

The solvent may be wholly or partly removed, for example, by distillation, optionally under reduced pressure and/or by azeotropic means with addition of water. The active substance (compound of the general formula (I)) may alternatively be isolated by precipitation by means of addition of nonsolvents such as aliphatic hydrocarbons, for example hexane, followed by separation by means of filtration and optionally drying. The active substance obtained by one of these methods can then be partly dissolved in a solvent suitable for the particular field of use or, if appropriate, be used in pure form, for example in powder coatings, or applied to inert supports. For applications in which the use of solids is preferred, such as powder coatings or particular plastics processing methods, the compounds can also be converted to a solid form by further known methods. Examples of such processes are microencapsulation, spray-drying, adsorption on a solid support such as $SiO_2$, or the PGSS (particles from gas saturated solutions) method.

Modifications

In a further embodiment, the XH groups still present in the inventive reaction product containing amido amine groups, i.e. OH groups and/or primary and/or secondary amino groups, can be converted further in a subsequent reaction, for example reacted with carboxylic anhydrides. In that case, the inventive reaction products containing amido amine groups serve as intermediates in the preparation of modified, likewise inventive reaction products containing amido amine groups. The modified products can be used in the same fields as the as yet unmodified inventive reaction products containing amido amine groups. The modification can, for example, increase or adjust the compatibility of the reaction products with respect to particular media.

The tertiary amino groups can also be converted to amine oxides with oxygen, peroxo compounds such as percarboxylic acids and with hydrogen peroxide, and these can additionally be converted to salts with acids, for example hydrochloric acid.

Salt Conversion Products

The inventive reaction products containing amido amine groups or the species of the general formula (I) present therein contain tertiary amino groups. All or some of these may be converted to salts. The tertiary amino groups may, for example, be converted to corresponding ammonium salts with acids such as carboxylic acids, carboxylic acid derivatives, for example carbonyl halides, or phosphoric acids and esters thereof. In that case, the inventive reaction products containing amido amine groups serve as intermediates in the preparation of likewise inventive reaction products containing amido amine groups that have been converted to salts. The products that have been converted to salts can be used in the same fields as the inventive reaction products containing amido amine groups that have not been converted to salts.

Conversion to salts can, for example, increase or adjust the compatibility of the reaction products with respect to particular media or affect the interaction with solid particles such as pigments and/or fillers.

Quaternization Products

The inventive reaction products containing amido amine groups or the species of the general formula (I) present therein contain tertiary amino groups. All or some of these may be converted to corresponding quaternary ammonium salts by reaction with quaternizing reagents. In that case, the inventive reaction products containing amido amine groups serve as intermediates in the preparation of quaternized, likewise inventive reaction products containing amido amine groups. The quaternized products can be used in the same fields as the unquaternized inventive reaction products containing amido amine groups. Quaternization can, for example, increase or adjust the compatibility of the reaction products with respect to particular media or affect the interaction with solid particles such as pigments and/or fillers.

Suitable quaternizing reagents may be chosen, for example, from the group of the alkyl halides and aralkyl halides or aralkyl compounds having leaving groups, such as triflate, methylsulfate or tosylate, which can enter into nucleophilic substitution reactions with tertiary amines, or oxiranes such as alkylene oxides or glycidyl ethers, in the presence of acids or derivatives thereof, such as carboxylic acids, sulfonic acids or phosphoric acids and the esters or halides thereof.

Examples of suitable quaternizing reagents are benzyl chloride, 2- or 4-vinylbenzyl chloride, methyl chloride, methyl iodide, methyl tosylate or dimethyl sulfate. Preference is given to benzyl chloride and 4-vinylbenzyl chloride.

A further means of quaternization is the use of glycidyl ethers in the presence of acids. Examples of suitable glycidyl ethers are glycidyl methacrylate, alkyl glycidyl ethers such as 2-ethylhexyl glycidyl ether and C13/C15 glycidyl ethers (trade name, for example, Grilonit RV 1814) or aryl glycidyl ethers such as cresyl glycidyl ether. Acids suitable for this quaternization reaction are, for example, carboxylic acids such as benzoic acid, acetic acid or lactic acid. Further acids are acidic phosphoric esters having one or two ester groups.

Inventive Use

The present invention further relates to the use of the above-described inventive reaction products containing amido amine groups or of the species of the general formula (I) present therein as an additive, preferably as a wetting agent and/or dispersant and/or dispersion stabilizer in compositions such as solid blends or coatings, especially varnishes, plastics, pigment pastes, sealants, cosmetics, ceramics, adhesives, potting compounds, spackling compounds, printing inks and other inks.

The invention also relates to the compositions detailed above, such as solid blends or coatings, especially varnishes, plastics, pigment pastes, sealants, cosmetics, ceramics, adhesives, potting compounds, spackling compounds, printing inks and other inks. The solid blends contain particles and/or fibers that have been treated with the above-described inventive reaction products containing amido amine groups or the species of the general formula (I) that are present therein.

The inventive reaction products containing amido amine groups or the species of the general formula (I) that are present therein find use, for example, as aluminum passivators, dispersants, dispersion stabilizers or wetting agents and can be used, for example, in pigmented and/or filler-containing products, for example pigment concentrates or pastes, coating compositions, sealants, plastics, ceramics, cosmetics, adhesives, potting compounds, spackling compounds, printing inks and/or other inks. Preference is given to pigment concentrates which can be mixed with appropriate letdown systems, by means of which pigmented varnishes are produced.

For example, the inventive reaction products containing amido amine groups or the species of the general formula (I) that are present therein may be used, for example, in the production or processing of varnishes, printing inks, other inks, for example for inkjet printing, paper coating, leather and textile dyes, pastes, pigment concentrates, ceramics, adhesives and sealants, potting compounds, plastics and cosmetic formulations, especially when these contain solids such as pigments and/or fillers (including fibrous fillers).

It is also possible to use these in the production or processing of molding compounds based on synthetic, semisynthetic or natural macromolecular substances, such as polyvinyl chloride, saturated or unsaturated polyesters, polyurethanes, polystyrenes, polyacrylates, polyamides, epoxy resins, polyolefins such as polyethylene or polypropylene. For example, these can be used for production of potting compounds, casting compounds, PVC plastisols, gelcoats, polymer concrete, printed circuit boards, industrial varnishes, wood and furniture varnishes, motor vehicle paints, marine paints, anticorrosion paints, can and coil coatings or decorating paints and architectural paints.

The inventive reaction products containing amido amine groups or the species of the general formula (I) that are present therein can be used not just in letdown systems for pigmented varnishes. It is likewise possible to use them in a wide range of formulations or products, such as resins, oils, greases, lubricants, rubber materials, sealants, printing inks, other inks, adhesives, waxes or coating compositions. The concentrates can also be used in formulations which are produced in the personal care industry or in electrical applications in the electronics industry, in the marine industry, in the context of medical applications, in the construction industry or in the automobile industry. Examples include electronic paper, such as the display in E-books, the encapsulation of microelectronic chips and printed circuit boards, underwater skin coatings for ships, such as antifouling coatings, silicone tubes or sliding additives for brake components.

The inventive reaction products containing amido amine groups or the species of the general formula (I) that are present therein can advantageously also be used in the production of color filters for liquid-crystal displays, liquid-crystal screens, color resolution devices, sensors, plasma screens, SED-based displays (Surface conduction Electron emitter Display), and for MLCCs (multilayer ceramic compounds). MLCC technology is employed in the production of microchips and printed circuit boards.

Use in cosmetic preparations can serve, for example, for production of cosmetic formulations such as makeup, face powder, lipsticks, hair dyes, creams, nail varnishes and sunscreen preparations. These may be in the customary forms, for example in the form of W/O or O/W emulsions, solutions, gels, creams, lotions or sprays. The inventive reaction products containing amido amine groups or the species of the general formula (I) that are present therein can advantageously be used in dispersions used for production of these formulations. These may comprise the carrier media that are customary for these purposes in cosmetics, such as water, castor oils or silicone oils, and solids such as organic and inorganic pigments, such as titanium dioxide or iron oxide.

Mention should likewise be made of the fields of use of NIP (nonimpact printing), inkjet printing (on paper, film, ceramic or synthetic and natural fiber fabric), dispersing of ceramics (in aqueous or anhydrous form), dispersing in potting compounds. The inventive reaction products containing amido amine groups or the species of the general formula (I) that are present therein may also be used in the aforementioned formulations and fields of use as they are, i.e. without having been incorporated into an appropriate concentrate beforehand.

Typically, the product comprising the inventive reaction products containing amido amine groups or the species of the general formula (I) that are present therein and also pigments and/or fillers is a varnish, or a pigment concentrate for coating compositions. Ultimately, however, it is possible to use the inventive reaction products containing amido amine groups or the species of the general formula (I) that are present therein in any pigment-containing and/or filler-containing products.

More particularly, the pigment concentrates are compositions which, as well as the inventive reaction products containing amido amine groups or the species of the general formula (I) that are present therein, comprise, for example, organic solvents and at least one pigment. The latter especially contain only small proportions, if any, of organic polymers as binders. Known binders of this kind are advantageously present in the corresponding letdown systems and are described hereinafter.

Organic solvents used are especially the typical organic solvents that are known to the person skilled in the art and are used in the field of the coatings and paints industry, such as aliphatic solvents, cycloaliphatic solvents, aromatic solvents such as toluene, xylene, solvent naphtha, ethers, esters and/or ketones, for example butyl glycol, butyl diglycol, butyl acetate, methyl isobutyl ketone, methyl ethyl ketone and/or solvents such as methoxypropyl acetate, diacetone alcohol.

Pigments used are the pigments known to those skilled in the art. Frequently, combinations of various pigments are used to obtain the desired properties. Examples of pigments are monoazo, diazo, triaand polyapigments, oxazine pigments, dioxazine pigments, thiazine pigments, diketopyrrolopyrroles, phthalocyanines, ultramarine and other metal complex pigments, indigoid pigments, diphenylmethane pigments, triarylmethane pigments, xanthene pigments, acridine pigments, quinacridone pigments, methine pigments, anthraquinone, pyranthrone pigments and perylene pigments and other polycyclic carbonyl pigments, inorganic pigments such as carbon black pigments and/or pigments based on carbon black, graphite, zinc, titanium dioxide, zinc oxide, zinc sulfide, zinc phosphate, barium sulfate, lithopone, iron oxide, ultramarine, manganese phosphate, cobalt aluminate, cobalt stannate, cobalt zincate, antimony oxide, antimony sulfide, chromium oxide, zinc chromate, mixed metal oxides based on nickel, bismuth, vanadium, molybdenum, cadmium, titanium, zinc, manganese, cobalt, iron, chromium, antimony, magnesium, aluminum (for example nickel titanium yellow, bismuth vanadate molybdate yellow or chromium titanium yellow), magnetic pigments based on pure iron, iron oxides and chromium oxides or mixed oxides, metal effect pigments comprising aluminum, zinc, copper or brass and also pearlescent pigments or fluorescent and phosphorescent luminous pigments. Further examples are nanoscale organic or inorganic solids having particle sizes below 100 nm in at least one dimension, such as certain types of carbon black or other allotropic forms of carbon, such as single-wall CNTs, multiwall CNTs and graphene. The particle size is determined, for example, by means of transmission electron microscopy, analytical ultracentrifugation or methods of light scattering. Mention should likewise be made of particles consisting of a metal or semimetal oxide or hydroxide, and also particles consisting of mixed metal and/or semimetal oxides or hydroxides. For example, the oxides and/or oxide hydroxides of aluminum, silicon, zinc, titanium, etc., can be used to produce such extremely finely divided solids. These oxide or hydroxide or oxide-hydroxide particles can be produced by a wide variety of different processes, for example ion exchange processes, plasma processes, sol-gel processes, precipitation, comminution (for example by grinding) or flame hydrolysis. All the aforementioned pigments may be in surface-modified form and have basic, acidic or neutral groups at the surface.

Further examples are the following pigments listed under their Color Index number (C.I.):

Examples of red pigments are C. I. Pigment Red 1, 2, 3, 4, 5, 6, 7, 8, 9, 12, 14, 15, 16, 17, 21, 22, 23, 31, 32, 37, 38, 41, 47, 48, 48:1, 48:2, 48:3, 48:4, 49, 49:1, 49:2, 50:1, 52:1, 52:2, 53, 53:1, 53:2, 53:3, 57, 57:1, 57:2, 58:4, 60, 63, 63:1, 63:2, 64, 64:1, 68, 69, 81, 81:1, 81:2, 81:3 ,81:4, 83, 88, 90:1, 101, 101:1, 104 ,108, 108:1, 109, 112, 113, 114, 122, 123, 144, 146, 147, 149, 151, 166, 168, 169, 170, 172, 173, 174, 175, 176, 177, 178, 179, 181, 184, 185, 187, 188, 190, 193, 194, 200, 202, 206, 207, 208, 209, 210, 214, 216, 220, 221, 224, 230, 231, 232, 233, 235. 236, 237, 238, 239, 242, 243, 245, 247, 249, 250, 251, 253, 254, 255, 256, 257, 258, 259, 260, 262, 263, 264, 265, 266, 267, 268, 269, 270, 271, 272, 273, 274, 275, and 276.

Examples of blue pigments are C. I. Pigment Blue 1, 1:2, 9, 14, 15, 15:1, 15:2, 15:3, 15:4, 15:6, 16, 17, 19, 25, 27, 28, 29, 33, 35, 36, 56, 56:1, 60, 61, 61:1, 62, 63, 66, 67, 68, 71, 72, 73, 74, 75, 76, 78, and 79.

Examples of green pigments are C. I. Pigment Green 1, 2, 4, 7, 8, 10, 13, 14, 15, 17, 18, 19, 26, 36, 45, 48, 50, 51, 54, 55, 58 or 59.

Examples of yellow pigments are C. I. Pigment Yellow 1, 1:1, 2, 3, 4, 5, 6, 9, 10, 12, 13, 14, 16, 17, 24, 31, 32, 34, 35, 35:1, 36, 36:1, 37, 37:1, 40, 41, 42, 43, 48, 53, 55, 61, 62, 62:1, 63, 65, 73, 74, 75, 81, 83, 87, 93, 94, 95, 97, 100, 101, 104, 105, 108, 109, 110, 111, 116, 117, 119, 120, 126, 127, 127:1, 128, 129, 133, 134, 136, 138, 139, 142, 147, 148, 150, 151, 153, 154, 155, 157, 158, 159, 160, 161, 162, 163, 164, 165, 166, 167, 168, 169, 170, 172, 173, 174, 175, 176, 180, 181, 182, 183, 184, 185, 188, 189, 190, 191, 191:1, 192, 193, 194, 195, 196, 197, 198, 199, 200, 202, 203, 204, 205, 206, 207, and 208.

Examples of violet pigments are C. I. Pigment Violet 1, 1:1, 2, 2:2, 3, 3:1, 3:3, 5, 5:1, 14, 15, 16, 19, 23, 25, 27, 29, 31, 32, 37, 39, 42, 44, 47, 49, and 50.

Examples of orange pigments are C. I. Pigment Orange 1, 2, 5, 13, 16, 17, 19, 20, 21, 22, 23, 24, 34, 36, 38, 39, 43, 46, 48, 49, 61, 62, 64, 65, 67, 68, 69, 70, 71, 72, 73, 74, 75, 77, 78, and 79.

Examples of black pigments are C. I. Pigment Black 7, 11, 30, 33.

If the respective products, especially the coating compositions, comprise fillers, is these are, for example, the fillers known to those skilled in the art. Examples of pulverulent or fibrous fillers are, for example, those formed from pulverulent or fibrous particles of aluminum oxide, aluminum hydroxide, silicon dioxide, kieselguhr, siliceous earth, quartz, silica gel, talc, kaolin, mica, perlite, feldspar, ground shale, calcium sulfate, barium sulfate, calcium carbonate, calcite, dolomite, glass or carbon. The fibers used may be organic and/or inorganic in nature and may likewise be used as reinforcing agents. Further examples of pigments or fillers can be found, for example, in U.S. Pat. No. 4,795,796. It is likewise also possible for flame retardants, if the compounds of the invention are not already being used in customary additive amounts for this purpose, such as aluminum hydroxide or magnesium hydroxide, and flatting agents, such as silicas, to be dispersed and stabilized particularly efficiently by means of the inventive reaction products containing amido amine groups or the species of the general formula (I) that are present therein.

The inventive reaction products containing amido amine groups or the species of the general formula (I) that are present therein are especially also suitable for production of solids concentrates, such as pigment concentrates. For this purpose, the inventive reaction products containing amido amine groups or the species of the general formula (I) that are present therein are initially charged in a carrier medium, such as organic solvents, plasticizers and/or water, and the solids to be dispersed are added while stirring. In addition, these concentrates may comprise binders and/or other auxiliaries. However, it is especially possible to use the inventive reaction products containing amido amine groups or the species of the general formula (I) that are present therein to produce stable binder-free pigment concentrates. It is likewise possible to use the inventive reaction products containing amido amine groups or the species of the general formula (I) that are present therein to produce free-flowing solids concentrates from pigment presscakes. This is done by mixing the inventive reaction products containing amido amine groups or the species of the general formula (I) that are present therein into the presscake, which may still comprise organic solvents, plasticizers and/or water, and dispersing the mixture thus obtained. The solids concentrates produced in various ways can then be incorporated into different substrates, for example alkyd resins, polyester resins, acrylate resins, polyurethane resins or epoxy resins. Pigments can alternatively be dispersed in a solvent-free manner directly into the inventive reaction products containing amido amine groups or the species of the general formula (I) that are present therein, and are then particularly suitable for pigmentation of thermoplastic and thermoset plastics formulations.

Use Amounts

According to the field of use, the inventive reaction products containing amido amine groups or the species of the general formula (I) that are present therein are used in such amounts that, in the product of ultimate interest for further use, there is preferably a proportion of the wetting agent and dispersant of the invention, the inventive reaction products containing amido amine groups or the species of the general formula (I) present therein, of 0.01% to 10% by weight, based on the total amount of the respective product. Alternatively, higher proportions are possible.

Based on the solids to be dispersed, for example the pigment, the inventive reaction products containing amido amine groups or the species of the general formula (I) that are present therein are used in an amount of preferably 0.5% to 100% by weight. If solids that are difficult to disperse are used, the amount of wetting agent and dispersant of the invention used, the inventive reaction products containing amido amine groups or the species of the general formula (I) present therein, may quite possibly be higher. The amount is generally dependent on the surface area of the substance to be dispersed which is to be covered. A factor of significance may thus, for example, be what kind of pigment is involved. In general, it can be stated that less dispersant is usually needed for dispersion of inorganic pigments than for organic pigments, since the latter usually have a higher specific surface area and therefore a greater amount of dispersant is needed. Typical dosages of the wetting agent and dispersant, i.e. the inventive reaction products containing amido amine groups or the species of the general formula (I) that are present therein, are, for example, 1% to 20% by weight for inorganic pigments and 10% to 50% by weight for organic pigments, based in each case on the solids to be dispersed, especially the pigment.

In the case of very finely divided pigments (for example some carbon blacks), even added amounts of 30% to 90% or more may be advisable. Criteria employed for sufficient pigment stabilization may, for example, be gloss and transparency of the coating compositions or the degree of floating. The dispersion of the solids can be effected in the form of an individual dispersion or else as a mixed dispersion with multiple pigments at the same time, the best results generally being achievable in individual dispersions. In the case of use of mixtures of different solids, opposing charges on the surfaces of the solids may result in increased agglomeration in the liquid phase. In these cases, when the inventive reaction products containing amido amine groups or the species of the general formula (I) that are present therein are used, it is frequently possible to achieve the same charge, generally a positive charge, of all particles and hence to avoid instabilities resulting from differences in charge. The dispersants, i.e. the inventive reaction products containing amido amine groups or the species of general formula (I) that are present therein, achieve their optimal effect when added to the millbase, especially when the solid to be dispersed is at first mixed solely with the additive and optionally solvents ("premix"), since the additive can then be preferably adsorbed onto the surface of the solids without having to compete with the binder polymers. In practice, however, this course of action is necessary only in exceptional cases. If required, the inventive reaction products containing amido amine groups or the species of the general formula (I) that are present therein can also be used subsequently (as what are called "post-additives"), for example in order to solve floating or flocculation problems in a batch that has already been let down. In general, however, elevated additive dosages are required in this case.

The products, especially the coating compositions or varnishes in which the inventive reaction products containing amido amine groups or the species of the general formula (I) that are present therein are ultimately to display their effects, may additionally comprise an organic polymer as a further binder. Binders of this kind are known to those skilled in the art. This at least one further binder may be introduced, for example, via a letdown system which is mixed, for example, with a pigment concentrate comprising the inventive reaction products containing amido amine groups or the species of the general formula (I) that are present therein, such that the io product in question is a pigmented varnish. Alternatively, other pigmented and/or filler-containing products are possible, for example plastics, sealants and further products based on an organic polymeric matrix that are known to those skilled in the art. A product is considered to be a system which comprises a polymeric resin or organic polymer as binder and hence is capable of forming a solid organic, polymeric is matrix under suitable curing conditions (for example a coating composition). A product likewise refers to a system which, through simple mixing with a component comprising a binder, is capable of forming such an organic polymeric matrix (for example a pigment concentrate). Nonexclusive examples of materials used include the alkyd resins, polyester resins, acrylate resins, polyurethane resins, cellulose nitrates, cellulose acetobutyrates, melamines, chloro rubbers and/or epoxy resins that are known to those skilled in the art. Examples of water-based coatings are cathodic or anodic electrocoats, for example for automobile bodywork. Further examples are renders, silicate paints, disperse dyes, water-based varnishes based on water-thinnable alkyds, alkyd emulsions, hybrid systems, 2-component systems, polyurethane dispersions and acrylate dispersions.

Both 1-component systems and 2-component systems are possible, in which latter case there are generally also polyisocyanates, melamine resins and/or polyamide resins present as the typical crosslinking agents familiar to the person skilled in the art in a second component. Preference is given to product systems, especially coating compositions, comprising an acrylate resin as binder. A further variant concerns a 2-component (2K) coating composition or a 2K varnish comprising an epoxy resin in the binder component and a polyamide resin in the crosslinker component.

The coating compositions that are preferred as products may be water-based or solvent-based. 'Water-based' is understood to mean that the coating composition comprises mainly water as solvent. More particularly, in the case of a water-based coating composition, preferably not more than 10% by weight of organic solvents, s based on the total amount of solvents, is present in the coating composition. A solvent-based coating composition is considered to be one that contains not more than 5% by weight, preferably not more than 2% by weight, of water, based on the total amount of solvents.

Useful further product components include, for example, photoinitiators, defoamers, wetting agents, film-forming auxiliaries, such as cellulose derivatives (for example cellulose nitrates, cellulose acetates, cellulose acetobutyrate), reactive diluents, leveling agents, dispersants and/or rheology control additives.

The production of the pigment concentrates and coating composition that are preferred as products is effected via methods familiar to those skilled in the art. The known methods are used, for example stepwise addition with stirring and mixing of the constituents of the coating composition in customary mixing units, such as stirred tanks or dissolvers.

Using the preferred pigment concentrates and coating compositions, it is possible to produce coatings or varnish layers. The coating is produced via techniques of application to a substrate that are familiar to those skilled in the art and subsequent curing methods.

Application is effected, for example, by the known injecting, spraying, painting, rolling, pouring, impregnating and/or dipping methods. The application of the coating composition to a substrate is followed by curing or drying by standard methods. For example, the coating composition applied may be curable by physical drying, by thermal means and/or with application of actinic radiation (radiative curing), preferably UV radiation and electron beams. Thermal curing can be effected, for example, in the range from about 10° C. to about 400° C., according to the nature of the coating composition and/or the substrate. The duration of curing is also individually dependent, for example, on the nature of the curing method (thermal or actinic), the nature of the coating composition used and/or the substrates. The substrate here may be moving or else at rest.

As well as the above-described application as a dispersant and/or coating for pulverulent and fibrous solids, the inventive reaction products containing amido s amine groups or the species of the general formula (I) that are present therein may also be used as viscosity reducers and compatibilizers in synthetic resins. Examples of synthetic resins of this kind are what are called the "sheet molding compounds" (SMCs) and "bulk molding compounds" (BMCs), which consist of unsaturated polyester resins with a high filler and fiber content. The production and processing thereof is described by way of example in U.S. Pat. No. 4,777,195. A problem with SMC and BMC synthetic resin mixtures is that polystyrene (PS) is often added to the formulation in order to reduce shrinkage during the processing operation. PS is incompatible with the unsaturated polyester resins used, and the components separate. In the case of use of PS-filled SMC or BMC mixtures, the inventive reaction products containing amido amine groups or the species of the general formula (I) that are present therein, because of their good dispersion qualities, can bring about compatibilization between PS and unsaturated polyester resin, which increases the storage stability and processing reliability of such mixtures.

By means of the inventive reaction products containing amido amine groups or the species of the general formula (I) that are present therein, it is possible to achieve phase transfer effects, for example, in incompatible polyol mixtures, polyol-isocyanate mixtures or polyol-blowing agent mixtures (as used, for example, in polyurethane production).

The present invention is additionally elucidated hereinafter by examples which follow.

EXAMPLES

In the case of molecularly inhomogeneous substances, the stated molecular weights —hereinafter as already in the above description—are number-average values. The molecular weights or number-average molecular weights $M_n$, in the event that titratable hydroxyl or amino groups are present, are determined by end group determination via the finding of the OH number, the amine number or the NCO number.

Unless stated otherwise, figures in parts are parts by weight and figures in percent s are percent by weight.

Solids Content

The sample (2.0±0.1 g of test substance) is weighed into an aluminum dish that has been dried beforehand and dried in a drying cabinet at 150° C. for 10 minutes, cooled down in a desiccator, and then re-weighed. The residue corresponds to the solids content.

NCO Number

The free NCO content of the polyisocyanates being used and the course of reaction of the NCO additions is determined according to EN ISO 9369 by reaction with butylamine and subsequent titration of the excess of amine. These methods are also described in Saul Patai "The Chemistry of Cyanates and their Thioderivates", Part 1, Chapter 5, 1977.

OH Number

The OH number is determined according to DIN ISO 4629 by acetylation with an excess of acetic anhydride. Subsequently, the excess acetic anhydride is hydrolyzed to acetic acid by addition of water and back-titrated with ethanolic KOH solution. The OH number indicates the amount of KOH in mg equivalent to the amount of acetic acid bound in the acetylation of 1 g of substance.

Amine Number

The amine number (AN) is understood to mean the amount of KOH in mg corresponding to the amine content of 1 g of substance. The amine number is determined according to DIN 16945 by potentiometric titration with 0.1 N perchioric acid in acetic acid.

Starting Materials

TDI toluene 2,4-diisocyanate (Desmodur T100), % NCO=48.8; manufacturer: Bayer Material Science PMA methoxypropyl acetate (solvent), manufacturer: Dow Chemical Comp.

DBTL dibutyltin dilaurate, manufacturer: Merck

DMAPA N,N-dimethylaminopropylamine, manufacturer: Huntsman Corp.

TEA triethanolamine, manufacturer: BASF

DEA N,N-diethanolamine, manufacturer: BASF

EA ethanolamine, manufacturer: BASF

IPA 3-imidazolyl-1-propylamine, manufacturer: BASF

BDMAPA N,N-bis[3-(dimethylamino)propyl]amine=Jeffcat Z 130, manufacturer: Huntsman Corp.

DMAE N,N-dimethylaminoethanol, manufacturer: BASF

APDEA N-(3-aminopropyl)diethanolamine, TCI Deutschland GmbH

AEE 2-(2-aminoethoxy)ethanol, manufacturer: BASF

MA methyl acrylate, manufacturer: BASF

BA butylamine, manufacturer: BASF

BzA benzylamine, manufacturer: BASF

Grilonit RV 1814 $C_{13}/C_{15}$-alkyl glycidyl ether, manufacturer: EMS-Chemie

Preparation of the Polyether-polyester Y—OH 1, Mn 780

350 g of MPEG 350 (methoxy polyethylene glycol, Mn 350), 434 g of ε-caprolactone and 1 g of DBTL (dibutyltin dilaurate) are reacted at 160° C. until a solids content of >97% has been attained.

The OH number of the reaction product is 72 mg KOH/g.

The further monohydroxy-functional polyesters used as Y—OH are prepared in an analogous manner.

General Preparation Method for the Monoadducts M of the General Formula (III) (Table 1):

A four-neck flask provided with a stirrer, thermometer, dropping funnel, reflux condenser and nitrogen inlet tube is initially charged with 430 g of Desmodur T100 (TDI) (about 100% toluene 2,4-diisocyanate, NCO content=48.8) and 7 g of benzoyl chloride, and mixed thoroughly. X g of the alcohol component which is anhydrous, and alkali-free in the case of polyethers, are metered in gradually such that the temperature does not exceed 55° C. After the metered addition, the mixture is stirred at 55° C. for a further 3 hours. The excess TDI is removed from the reaction mixture by means of a thin-film evaporator at 150° C. The residual TDI content is <1%.

TABLE 1

Overview of the monoadducts M of the general formula (III)

| Mono-adduct | Alcohol component Y—OH | Amount X in [g] |
|---|---|---|
| M1 | n-Butanol-started PO polyether Mn 800, OH number: 70 mg KOH/g | 800 |
| M2 | MPEG 350, OH number: 160 mg KOH/g | 350 |
| M3 | n-Butanol-started EO/PO polyether (EO:PO 1:1) Mn 2240, OH number: 25 mg KOH/g | 2240 |
| M4 | Polyester Y—OH 1, OH number: 72 mg KOH/g | 780 |
| M5 | Hexadecanol-started monohydroxy-functional ε-caprolactone polyester, Mn 600 | 600 |
| M6 | Hexadecanol-started monohydroxy-functional ε-caprolactone polyester, Mn 1200 | 1200 |
| M7 | MPEG 500 = methoxy polyethylene glycol, Mn 500 | 500 |
| M8 | n-Butanol-started EO/PO polyether (EO:PO 1:1) Mn 1100 | 1100 |
| M9 | n-Butanol-started EO/PO polyether (EO:PO 1:1) Mn 1500 | 1500 |
| M10 | n-Butanol-started EO/PO polyether (EO:PO 1:1) Mn 1800 | 1800 |
| M11 | n-Butanol-started EO/PO polyether (EO:PO 1:1) Mn 3100 | 3100 |
| M12 | n-Butanol-started EO/PO polyether (EO:PO 1:1) Mn 4250 | 4250 |
| M13 | Monohydroxy-functional hydroxypropyl polydimethylsiloxane with butyl end group, Mn 1200 | 1200 |
| M14 | Methanol-started EO/PO polyether (EO:PO 3:1), Mn 1400 | 1400 |
| M15 | MPEG 500-started ε-caprolactone polyester Mn 900 | 900 |
| M16 | Isodecanol-started ε-caprolactone polyester Mn 700 | 700 |
| M17 | Isodecanol-started ε-caprolactone polyester Mn 1000 | 1000 |
| M18 | Monophenyl glycol-started ε-caprolactone polyester, Mn 1200 | 1200 |
| M19 | n-Butanol-started ε-caprolactone polyester, Mn 600 | 600 |
| M20 | n-Butanol-started ε-caprolactone polyester, Mn 1200 | 1200 |
| M21 | n-Butanol-started PO polyether, Mn 1100 | 1100 |
| M22 | Isodecanol-started polyester formed from ε-caprolactone and δ-valerolactone in a molar ratio of 3:1, Mn = 2000 | 2000 |
| M23 | ε-caprolactone polyester Mn 1950, started with an n-butanol-started EO/PO polyether (EO:PO 1:1), Mn 1500 | 1950 |
| M24 | MPEG 350-started ε-caprolactone polyester Mn 900 | 900 |
| M25 | MPEG 350-started polyester formed from ε-caprolactone and δ-valerolactone in a molar ratio of 3:1, Mn = 950 | 950 |
| M26 | MPEG 500-started polyester formed from ε-caprolactone and δ-valerolactone in a molar ratio of 3:1, Mn = 1100 | 1100 |
| M27 | MPEG 750-started polyester formed from ε-caprolactone and δ-valerolactone in a molar ratio of 3:1, Mn = 1400 | 1400 |
| M28 | MPEG 750 | 750 |
| M29 | ε-caprolactone polyester Mn 1630, started with a methanol-started EO/PO polyether (EO:PO 3:1), Mn 1400 | 1630 |

TABLE 1-continued

Overview of the monoadducts M of the general formula (III)

| Mono-adduct | Alcohol component Y—OH | Amount X in [g] |
|---|---|---|
| M30 | n-Butanol-started EO/PO polyether (EO:PO 1:1) Mn 2540 | 2540 |
| M31 | n-Butanol-started PO polyether, Mn 2240 | 2240 |
| M32 | n-Butanol-started butylene oxide polyether, Mn 960 | 960 |
| M33 | Oleyl alcohol | 268 |
| M34 | Monophenyl glycol | 138 |
| M35 | n-Decanol | 158 |

General Method for Preparation of the Amido Amines AA of the General Formula (IV):

First Step (Michael Addition) to give Intermediate I (Table 2):

A four-neck flask provided with a stirrer, thermometer, water separator and nitrogen inlet tube is initially charged with y g of the amine B and/or z g of the amino alcohol C at room temperature. Subsequently, x g of component A are added gradually, such that the reaction temperature does not exceed 35-40° C. The progress of the reaction is monitored by means of 1H NMR. The reaction is considered to have ended when the C=C double bond of the ethylenically unsaturated ester compound A has been fully converted.

Second Step (Amidation) to give Amido Amine AA (Table 3)

On completion of conversion of the C=C double bond of the ethylenically unsaturated ester compound A in the first step, the ester group of the intermediate I obtained is amidated with a primary or secondary amino group of an amine component B and/or C, by heating the Michael adduct to 80° C. and adding the amine B and/or C to the reaction mixture at 80° C. and then increasing the temperature stepwise to 120° C. For better removal of the alcohol formed from the reaction mixture, a reduced pressure of 500 mbar is applied after one hour of reaction time at 120° C. The reaction mixture is stirred under these conditions until monitoring of the reaction by infrared spectroscopy shows complete conversion of the ester groups to amide groups. Dilution with PMA is optionally possible after the reaction.

Preparation of the Intermediates I:

TABLE 2

Preparation of the intermediates I

| Example | Amount x of component A | Amount y of component B | Amount z of component C |
|---|---|---|---|
| I1 | 86 g MA | | 105 g DEA |
| I2 | 172 g MA | 73 g BA | |
| I3 | 172 g MA | 107 g BzA | |
| I4 | 86 g MA | 187 g BDMAPA | |
| I5 | 172 g MA | | 105 g AEE |
| I6 | 172 g MA | | 61 g EA |
| I7 | 172 g MA | | 162 g APDEA |
| I8 | 172 g MA | 102 g DMAPA | |

DEA = N,N-diethanolamine,
MA = methyl acrylate,
BA = butylamine,
BzA = benzylamine,
BDMAPA = N,N-bis[3-(dimethylamino)propyl]amine,
AEE = 2-(2-aminoethoxy)ethanol,
EA = ethanolamine,
APDEA = N-(3-aminopropyl)diethanolamine,
DMAPA = N,N-dimethylaminopropylamine Preparation of the Amido Amines AA:

TABLE 3

Preparation of the amido amines AA

| Example | Amount x of I | Amount y of B | Amount z of C |
|---|---|---|---|
| AA1 | 197 g I1 | 102 g DMAPA | |
| AA2 | 197 g I1 | 125 g IPA | |
| AA3 | 223 g I6 | 204 g DMAPA | |
| AA4 | 236 g I2 | | 122 g EA |
| AA5 | 236 g I2 | | 210 g DEA |
| AA6 | 265 g I3 | | 122 g EA |
| AA7 | 265 g I4 | | 105 g DEA |
| AA8 | 320 g I7 | 204 g DMAPA | |
| AA9 | 263 g I5 | 204 g DMAPA | |
| AA10 | 197 g I1 | 187 g BDMAPA | |
| AA11 | 266 g I8 | | 122 g EA |
| AA12 | 266 g I8 | | 324 g APDEA |
| AA13 | 223 g I6 | | 324 g APDEA |
| AA14 | 320 g I7 | | 324 g APDEA |
| AA15 | 223 g I6 | 102 g DMAPA | 61 g EA |
| AA16 | 223 g I6 | 102 g DMAPA | 162 g APDEA |

DMAPA = N,N-dimethylaminopropylamine,
IPA = 3-imidazolyl-1-propylamine,
EA = ethanolamine,
DEA = N,N-diethanolamine,
BDMAPA = N,N-bis[3-(dimethylamino)propyl]amine,
APDEA = N-(3-aminopropyl)diethanolamine General Method for Step ii) for Conversion of the Monoadducts M of the General Formula (III) to Reaction Products Containing Amido Amine Groups of the General Formula (I):

In One Single Stage ii-a) (Table 4):

A four-neck flask equipped with a stirrer, thermometer, dropping funnel, reflux condenser and nitrogen inlet tube is initially charged with y g of the amido amine AA and heated to 70° C. while stirring under nitrogen. Subsequently, x g of monoadduct are added gradually, such that the reaction temperature does not exceed 80° C. Subsequently, the reaction mixture is stirred at 80° C. until the isocyanate has reacted to completion. The progress of the reaction is followed by means of titrimetric determination of the NCO number to EN ISO 9369. The reaction is considered to have ended when an NCO content of <0.1% is determined. Dilution with PMA is optionally possible during or after the reaction.

When any hydroxyl groups present in the amido amine AA are to be reacted with a monoadduct M of the general formula (III), the reaction is effected with addition of 200 ppm of dibutyltin dilaurate; otherwise, the preparation is conducted as described.

TABLE 4

Reaction of the monoadducts M with amido amines AA in step ii-a)

| Example | Amount x of monoadduct M | Amount y of amido amine AA | PMA in g | Solids in % |
|---|---|---|---|---|
| P1 | 127.4 g M21 | 26.1 g AA1 | | 97.8 |
| P2 | 197.4 g M10 | 26.1 g AA1 | | 98.2 |
| P3 | 442.4 g M12 | 26.1 g AA1 | 468.5 g | 49.5 |
| P4 | 334.8 g M9 | 26.1 g AA1 | | 98.6 |
| P5 | 167.4 g M9 | 38.6 g AA3 | | 98.4 |
| P6 | 97.4 g M1 | 38.6 g AA3 | | 97.9 |
| P7 | 241.4 g M3 | 38.6 g AA3 | | 99.2 |
| P8 | 67.4 g M7 | 38.6 g AA3 | | 97.3 |
| P9 | 157.4 g M14 | 38.6 g AA3 | | 98.5 |
| P10 | 107.4 g M15 | 38.6 g AA3 | | 98.7 |
| P11 | 334.8 g M9 | 27.6 g AA2 | | 97.6 |
| P12 | 167.4 g M9 | 27.6 g AA2 | | 97.9 |
| P13 | 190.8 g M4 | 27.6 g AA2 | | 99.1 |
| P14 | 254.8 g M8 | 27.6 g AA2 | | 98.9 |
| P15 | 154.8 g M19 | 27.6 g AA2 | | 97.7 |
| P16 | 542.8 g M30 | 27.6 g AA2 | | 98.5 |
| P17 | 669.6 g M9 | 34.8 g AA5 | | 98.1 |
| P18 | 309.6 g M5 | 34.8 g AA5 | | 99.0 |
| P19 | 549.6 g M18 | 34.8 g AA5 | | 98.8 |
| P20 | 412.2 g M18 | 34.8 g AA5 | | 98.3 |
| P21 | 274.8 g M18 | 34.8 g AA5 | | 97.6 |
| P22 | 137.4 g M18 | 34.8 g AA5 | | 97.1 |
| P23 | 629.6 g M27 | 34.8 g AA5 | 664.4 g | 48.7 |
| P24 | 124.8 g M34 | 34.8 g AA5 | | 97.8 |
| P25 | 334.8 g M9 | 30.6 g AA6 | | 98.4 |
| P26 | 274.8 g M6 | 30.6 g AA6 | | 98.8 |
| P27 | 104.8 g M2 | 30.6 g AA6 | | 98.0 |
| P28 | 226.8 g M32 | 30.6 g AA6 | | 98.1 |
| P29 | 88.4 g M33 | 30.6 g AA6 | | 97.9 |
| P30 | 254.8 g M8 | 30.6 g AA6 | | 97.4 |
| P31 | 334.8 g M9 | 38.0 g AA10 | | 96.8 |
| P32 | 334.8 g M9 | 31.3 g AA4 | | 97.5 |
| P33 | 654.8 g M11 | 31.3 g AA4 | | 97.7 |
| P34 | 482.8 g M31 | 31.3 g AA4 | | 97.8 |
| P35 | 62.4 g M34 | 31.3 g AA4 | | 98.1 |
| P36 | 214.8 g M24 | 31.3 g AA4 | | 98.9 |
| P37 | 334.8 g M9 | 35.0 g AA7 | | 98.2 |
| P38 | 334.8 g M9 | 44.8 g AA8 | | 96.4 |
| P39 | 184.8 g M28 | 44.8 g AA8 | | 97.1 |
| P40 | 92.4 g M28 | 44.8 g AA8 | | 96.8 |
| P41 | 66.4 g M35 | 44.8 g AA8 | | 98.8 |
| P42 | 167.4 g M9 | 38.8 g AA9 | | 99.2 |
| P43 | 117.4 g M17 | 38.8 g AA9 | | 97.4 |
| P44 | 92.4 g M29 | 38.8 g AA9 | | 98.2 |
| P45 | 334.8 g M9 | 30.2 g AA11 | | 98.8 |
| P46 | 274.8 g M20 | 30.2 g AA11 | | 96.7 |
| P47 | 224.8 g M25 | 30.2 g AA11 | 255.0 g | 49.8 |
| P48 | 669.6 g M9 | 47.1 g AA12 | | 97.6 |
| P49 | 502.2 g M9 | 47.1 g AA12 | | 98.6 |
| P50 | 334.8 g M9 | 47.1 g AA12 | | 98.2 |
| P51 | 167.4 g M9 | 47.1 g AA12 | | 98.7 |
| P52 | 509.6 g M26 | 47.1 g AA12 | | 97.8 |
| P53 | 509.6 g M21 | 47.1 g AA12 | | 99.0 |
| P54 | 669.6 g M9 | 50.8 g AA13 | | 99.4 |
| P55 | 349.6 g M16 | 50.8 g AA13 | | 98.8 |
| P56 | 849.6 g M23 | 50.8 g AA13 | | 98.2 |
| P57 | 502.2 g M9 | 53.6 g AA14 | | 99.1 |
| P58* | 167.4 g M9 | 10.2 g DMAPA | | 98.4 |
| P59* | 167.4 g M9 | 8.9 g DMAE | | 96.5 |
| P60* | 167.4 g M9 | 18.7 g BDMAPA | | 97.6 |
| P61* | 167.4 g M9 | 14.9 g TEA | | 98.0 |
| P62 | 274.8 g M13 | 32.2 g AA15 | | 97.8 |
| P63 | 652.2 g M22 | 41.7 g AA16 | | 98.4 |

*noninventive examples/prior art
PMA = methoxypropyl acetate (solvent),
DMAPA = N,N-dimethylaminopropylamine,
TEA = triethanolamine,
DMAE = N,N-dimethylaminoethanol,
BDMAPA = N,N-bis[3-(dimethylamino)propyl]amine In a Stage Sequence ii-b) (Table 5):
First Step:

A four-neck flask equipped with a stirrer, thermometer, dropping funnel, reflux condenser and nitrogen inlet tube is initially charged with y g of the intermediate I and heated to 70° C. while stirring under nitrogen. Subsequently, x g of monoadduct M are added gradually, such that the reaction temperature does not exceed 80° C. Subsequently, the reaction mixture is stirred at 80° C. until the isocyanate has reacted to completion. The progress of the reaction is followed by means of titrimetric determination of the NCO number to EN ISO 9369. The reaction is considered to have ended when an NCO content of <0.1% is determined.

Second Step:

On completion of reaction of the isocyanate group with an alcohol group, a primary amino group or a secondary amino group of an intermediate I in the first step, the intermediate J obtained is amidated with a primary or secondary amino group of an amine component B and/or C, by adding the amine B and/or C to the reaction mixture at 80° C. and increasing the temperature stepwise to 120° C. For better removal of the alcohol formed from the reaction mixture, a reduced pressure of 500 mbar is applied after one hour of reaction time at 120° C. The reaction mixture is stirred under these conditions until monitoring of the reaction by infrared spectroscopy shows complete conversion of the ester group to the amide group. In the case of products containing polyester in the Y radical, such that it becomes more difficult to monitor the reaction by infrared spectroscopy, the end of the reaction is s determined in that no further alcohol forms; thus, the amidation is considered to have ended. Dilution with PMA is optionally possible after the reaction.

TABLE 5

Reaction of the monoadducts M with an intermediate I and subsequent amidation in step ii-b)

| Example | Amount x of monoadduct M | Amount y of intermediate I | Amount z of component B or C |
|---|---|---|---|
| P64 | 127.4 g M21 | 19.7 g I1 | 10.2 g DMAPA |
| P65 | 254.8 g M21 | 19.7 g I1 | 10.2 g DMAPA |
| P66 | 97.4 g M1 | 22.3 g I6 | 20.4 g DMAPA |
| P67 | 194.8 g M1 | 19.7 g I1 | 10.2 g DMAPA |
| P68 | 127.4 g M21 | 19.7 g I1 | 6.1 g EA |

DMAPA = N,N-dimethylaminopropylamine,
EA = ethanolamine

General Method for Quaternization (Table 6):

In a four-neck flask provided with a stirrer, thermometer, dropping funnel, reflux condenser and nitrogen inlet tube, y g of the starting compound in 170 g of PMA (methoxypropyl acetate) and 170 g of butylglycol and x g of alkylating reagent are reacted at 120° C. for 4 h. The solids content is adjusted to 40% with a 1:1 mixture of PMA and butylglycol.

TABLE 6

Quaternization

| Example | Amount y of starting compound | Amount x of alkylating reagent |
|---|---|---|
| Q1 | 224 g P2 | 6.9 g of benzyl chloride |
| Q2 | 224 g P2 | 14.7 g of Grilonit 1814<br>6.4 g of benzoic acid |
| Q3 | 224 g P2 | 9.5 g of benzyl chloride |
| Q4 | 224 g P2 | 26.7 g of Grilonit 1814<br>11.6 g of benzoic acid |
| Q5 | 224 g P2 | 12.0 g of benzyl chloride |

Grilonit RV 1814 = $C_{13}/C_{15}$-alkyl glycidyl ether, EMS-Chemie

General Method for Salt Formation (Table 7):

In a four-neck flask provided with a stirrer, thermometer, dropping funnel, reflux condenser and nitrogen inlet tube, y g of the compound to be converted to a salt in 170 g of PMA and 170 g of butylglycol is stirred with x g of salt conversion reagent at 60° C. for 1 h.

TABLE 7

Salt formation

| Example | Amount y of reaction product P | Amount x of salt conversion reagent |
|---|---|---|
| S1 | 224 g P2 | 14.6 g of adipic acid |
| S2 | 224 g P2 | 24.4 g of benzoic acid |
| S3 | 224 g P2 | 12.2 g of benzoic acid |
| S4 | 224 g P2 | 7.3 g of adipic acid |
| S5 | 224 g P2 | 28.2 g of oleic acid |
| S6 | 224 g P2 | 20.0 g of lauric acid |
| S7 | 224 g P2 | 29.8 g of ricinoleic acid |
| S8 | 224 g P2 | 9.0 g of lactic acid | c) Performance Testing

Use of the polymers of the invention as wetting agent and dispersing additive for production of pigment concentrates and use thereof in varnish systems Starting Materials

| | |
|---|---|
| Paraloid B-66 | thermoplastic acrylate resin, manufacturer: DOW Chemicals |
| Joncryl 500 | hydroxy-functional acrylic resin, manufacturer: BASF |
| Laropal A 81 | aldehyde resin, manufacturer: BASF |
| Cymel 303 | amino crosslinker, manufacturer: Allnex |
| MAK | methyl amyl ketone, manufacturer: Eastman |
| DIDP | diisodecyl phthalate |
| Nacure 2500 | p-toluenesulfonic acid, manufacturer: King Industries |
| Dowanol PMA | propylene glycol methyl ether acetate, manufacturer: Dow Chemicals |
| Raven 5000 Ultra III | carbon black pigment for high jetness, manufacturer |
| Paliogen Red L3880 HD | perylene red pigment, manufacturer |
| Hostaperm RL NF | violet pigment, manufacturer |
| Heliogen Blue L7101F | phthalocyanine blue (P.B. 15:4), manufacturer: BASF |
| Hostaperm Rosa E | quinacridone red (P.R. 122), manufacturer: Clariant |
| Colour Black FW 200 | carbon black pigment (P. Bk. 7), manufacturer: Orion |
| BYK 310 | substrate wetting agent, manufacturer: BYK-Chemie |
| BYK 306 | substrate wetting agent, manufacturer: BYK-Chemie |

Procedures

Production of Pigment Concentrates Based on a Thermoplastic Acrylate

The Paraloid B-66 dispersion resin, solvent, dispersing additive and pigment were weighed into 100 mL glass bottles so as to obtain 50 g of millbase. Subsequently, 50 g of glass beads (1 mm) were weighed in.

Composition of the TPA Pigment Concentrates (figures in g)

| | TPA 1 (black) | TPA 2 (red) | TPA 3 (violet) |
|---|---|---|---|
| Paraloid B-66 (50% in xylene) | 24.0 | 24.0 | 24.0 |
| Raven Ultra 5000 III | 6.0 | | |
| Paliogen Red L 3880 HD | | 8.0 | |
| Hostaperm RL-NF | | | 5.0 |
| Dispersing additive | 4.2 | 2.0 | 2.0 |
| n-Butanol | 5.0 | 5.0 | 5.0 |
| PMA | | 11.0 | 14.0 |
| Butyl acetate | 10.8 | | |
| Total pigment content (%) | 12 | 16 | 10 |
| Dispersant (% s.o.p.) | 70 | 25 | 40 |

Grinding Conditions:
Equipment: Lau Disperser DAS 200
Dispersing time: 300 min, cooling power at level 3
Ratio of millbase to glass beads (diameter 1 mm): 1:1 (parts by weight)
Assessment of Millbase Viscosity of the TPA Dispersions The millbase viscosity of the TPA dispersions was determined with a Rheological Stresstech Rheometer (plate/cone, 25 mm, 1°) at 23° C.

Millbase Viscosities

|  | TPA 1 (black) Raven 5000 Ultra III | | | TPA 2 (red) Paliogen Red L3880 HD Viscosity in Pa * s | | | TPA 3 (violet) Hostaperm RL-NF | | |
| --- | --- | --- | --- | --- | --- | --- | --- | --- | --- |
|  | 1/s | 10/s | 100/s | 1/s | 10/s | 100/s | 1/s | 10/s | 100/s |
| P59* | 45.890 | 7.727 | 1.828 | 15.370 | 2.876 | 0.814 | 42.110 | 4.786 | 1.085 |
| P60* | 48.380 | 7.022 | 1.663 | 15.440 | 2.879 | 0.864 | 38.460 | 4.680 | 1.005 |
| P61* | 51.610 | 7.534 | 1.774 | 22.470 | 3.808 | 1.011 | 57.960 | 7.762 | 1.432 |
| P4 | 12.200 | 2.688 | 1.048 | 7.456 | 1.722 | 0.657 | 35.530 | 4.294 | 0.970 |
| P11 | 24.470 | 4.746 | 1.419 | 9.462 | 1.881 | 0.677 | 37.990 | 4.614 | 0.968 |
| P17 | 32.960 | 6.113 | 1.631 | 6.069 | 1.586 | 0.685 | 36.670 | 4.508 | 0.982 |
| P25 | 18.390 | 3.661 | 1.132 | 8.977 | 1.888 | 0.688 | 39.180 | 4.647 | 1.027 |

The inventive dispersing additives P4, P11, P17 and P25 have a significant viscosity-reducing effect compared to the prior art P59*, P60* and P61* in TPA dispersions of 3 different pigments, which is manifested even at low shear rates.

Production of the TPA-based Letdown System

Paraloid B-66, solvent and leveling additive were weighed into a 2.5 L PE bucket and homogenized with a Dispermat CV (65 mm toothed disk) at 2000 rpm for 5 min.

Composition of the TPA Letdown System (figures in g)

| TPA clearcoat | Weight in g |
| --- | --- |
| Paraloid B-66 (50% in xylene) | 700 |
| DIDP | 20 |
| Xylene | 218 |
| PMA | 60 |
| BYK-306 | 2 |

Production of the Pigmented TPA Letdown Systems

The TPA letdown system and the TPA-based pigment dispersion were weighed into a PE cup and mixed with a spatula. Subsequently, all the final TPA letdown systems were homogenized in an ANDALOK shaker for 10 min.

Composition of the Pigmented TPA Letdown Systems (Figures in g)

|  | TPA-B1 | TPA-B2 | TPA-B3 |
| --- | --- | --- | --- |
| TPA letdown system | 28.0 | 27.0 | 26.0 |
| TPA 1 (black) | 2.0 |  |  |
| TPA 2 (red) |  | 3.0 |  |
| TPA 3 (violet) |  |  | 4.0 |
| Pigment content (%) | 0.8 | 1.6 | 1.3 |

Application and Evaluation of the Pigmented TPA Letdown Systems

The pigmented TPA letdown systems were bar-coated onto PE film (50 μm or 100 μm) and dried at 22° C. for 24 h. Subsequently, the haze and gloss were measured with a BYK micro haze plus instrument at an angle of 20°. In each case, low values for haze and high values for gloss are considered to be positive results. In addition, the optical color intensity and transparency through the drawdowns onto PE film was assessed using grades 1 (excellent) to 5 (unacceptable).

| TPA B1 (black) Raven 5000 Ultra III | | | |
| --- | --- | --- | --- |
| Dispersing additive in the millbase | Masstone 100 μm PE film Haze | Masstone 100 μm PE film Gloss 20° | Masstone 100 μm PE film Transparency/color intensity |
| P59* | 11 | 80 | 2-3 |
| P60* | 21 | 78 | 4 |

-continued

| TPA B1 (black) Raven 5000 Ultra III | | | |
| --- | --- | --- | --- |
| Dispersing additive in the millbase | Masstone 100 μm PE film Haze | Masstone 100 μm PE film Gloss 20° | Masstone 100 μm PE film Transparency/color intensity |
| P61* | 12 | 80 | 3 |
| P4 | 11 | 80 | 2-3 |
| P11 | 10 | 81 | 2 |
| P17 | 10 | 82 | 1-2 |
| P25 | 11 | 80 | 2 |

| TPA B2 (red) Paliogen Red L3880 HD | | | |
| --- | --- | --- | --- |
| Dispersing additive in the millbase | Masstone 100 μm PE film Haze | Masstone 100 μm PE film Gloss 20° | Masstone 50 μm PE film Transparency/color intensity |
| P59* | 13 | 77 | 3-4 |
| P61* | 20 | 73 | 4 |
| P4 | 11 | 80 | 3 |
| P17 | 12 | 79 | 3 |

| TPA B3 (violet) Hostaperm RL-NF | | | |
| --- | --- | --- | --- |
| Dispersing additive in the millbase | Masstone 50 μm PE film Haze | Masstone 50 μm PE film Gloss 20° | Masstone 50 μm PE film Transparency/color intensity |
| P59* | 43 | 71 | 3-4 |
| P61* | 45 | 71 | 3 |
| P4 | 36 | 74 | 2-3 |
| P25 | 36 | 75 | 2-3 |

The dispersing additives of the invention exhibit lower haze, better gloss values and higher transparency and color intensity compared to the prior art for TPA-based varnish systems.

Production of the Laropal A81 Pigment Dispersion

The Laropal A81 dispersion resin (60 parts) was weighed into a 2.5 L PE bucket together with PMA (40 parts) and homogenized by means of a Dispermat CV (65 mm toothed disk) at 2000 rpm for 30 min. Subsequently, the solution of the dispersion resin, solvent, dispersing additive and pigment was weighed into 100 mL glass bottles so as to obtain 50 g of millbase. Subsequently, 50 g of glass beads (1 mm) were weighed in.

Composition of the Laropal A81 Pigment Concentrates (Figures in g)

|  | LA 1 (black) | LA 2 (pink) | LA 3 (blue) |
| --- | --- | --- | --- |
| Laropal A 81 (60% in PMA) | 8.7 | 20.4 | 21.9 |
| Colour Black FW 200 | 4.0 | | |
| Hostaperm Pink E | | 7.0 | |
| Heliogen Blue 7101F | | | 7.5 |
| Dispersing additive | 2.8 | 1.8 | 1.9 |
| PMA | 34.5 | 20.8 | 18.7 |
| Total pigment content (%) | 8 | 14 | 15 |
| Dispersant (% s.o.p.) | 70 | 25 | 25 |

Grinding Conditions:
Equipment: Lau Disperser DAS 200
Grinding time: 300 min, cooling power at level 3
Ratio of millbase to glass beads (diameter 1 mm): 1:1 (parts by weight)

Assessment of the Millbase Viscosity and the Laropal A81 Dispersions

The millbase viscosity of the Laropal A81 dispersions was determined with a Rheological Stresstech Rheometer (plate/cone, 25 mm, 1°) at 23° C.

Millbase Viscosities

| | LA 1 (black) Viscosity in mPa * s | | | LA 2 (pink) Viscosity in mPa * s | | | LA 3 (blue) Viscosity in mPa * s | | |
| --- | --- | --- | --- | --- | --- | --- | --- | --- | --- |
| | 1/s | 10/s | 100/s | 1/s | 10/s | 100/s | 1/s | 10/s | 100/s |
| P58* | 44 | 13 | 10 | 34870 | 3934 | 794 | 9457 | 1017 | 214 |
| P60* | 185 | 86 | 34 | 28460 | 3656 | 939 | 10450 | 1474 | 228 |
| P61* | 232 | 25 | 9 | 33660 | 3399 | 995 | 10720 | 815 | 247 |
| P4 | 26 | 12 | 9 | 25750 | 2907 | 519 | 6646 | 894 | 179 |
| P11 | 36 | 12 | 9 | 24990 | 3252 | 519 | 6072 | 827 | 172 |
| P17 | 19 | 11 | 9 | 18400 | 1857 | 381 | 7889 | 905 | 202 |
| P25 | 31 | 13 | 9 | 25230 | 2841 | 555 | 6862 | 921 | 184 |

Production of a Baking Varnish JC1

Binder, solvent and substrate wetting agent were weighed into a 2.5 L PE bucket and homogenized with a Dispermat CV (65 mm toothed disk) at 2000 rpm for 5 min.

Composition of the Baking Varnish JC1 (Figures in g)

| Baking varnish JC1 | Weight in g |
| --- | --- |
| Joncryl 500 | 576.0 |
| Cymel 303 | 198.0 |
| Butanol | 80.0 |
| MAK | 130.0 |
| BYK-310 | 3.0 |
| Nacure 2500 | 13.0 |

Production of Various Varnishes Based on the Laropal A81 Pigment Dispersions

The Laropal A81-based pigment dispersions and the baking varnish JC1 were weighed into a PE cup and mixed by hand with a spatula. Subsequently, the pigmented varnishes were homogenized in an ANDALOK shaker for 10 min.

Composition of the Pigmented JC1 Letdown Systems (Figures in g)

|  | JC1-B1 (black) | JC1-B2 (pink) | JC1-B3 (blue) |
| --- | --- | --- | --- |
| JC1 | 18.0 | 17.9 | 16.0 |
| LA 1 (black) | 2.0 | | |
| LA 2 (pink) | | 2.1 | |
| LA 3 (blue) | | | 4.0 |
| Pigment content (%) | 0.8 | 1.5 | 3.0 |

Application and evaluation of the pigmented baking varnishes JC1-B1 to JC1-B3

The pigmented baking varnishes JC1-B1-B3 were bar-coated onto PE film (50 μm), flashed off at 22° C. for 15 min and baked at 150° C. for 20 min. Subsequently, haze and gloss were measured with a BYK micro haze plus instrument at an angle of 20°. In each case, low values for haze and high values for gloss are considered to be positive results. In addition, the optical transparency and color intensity through the drawdowns onto PE film was assessed using grades 1 (excellent) to 5 (unacceptable).

Comparison of the Black Baking Varnishes JC1-B1 (Black)

| Synthesis name | Gloss 20° | Haze | Transparency/ color intensity |
| --- | --- | --- | --- |
| P58* | 106 | 11 | 4 |
| P60* | 103 | 24 | 3-4 |

-continued

| Synthesis name | Gloss 20° | Haze | Transparency/ color intensity |
| --- | --- | --- | --- |
| P61* | 105 | 14 | 1-2 |
| P4 | 106 | 14 | 1 |
| P11 | 105 | 10 | 1 |
| P17 | 106 | 16 | 1 |
| P25 | 107 | 10 | 2 |

Comparison of the Pink Baking Varnishes JC1-B2 (Pink)

| Synthesis name | Gloss 20° | Haze | Transparency/color intensity |
|---|---|---|---|
| P59* | 112 | 33 | 3 |
| P60* | 113 | 19 | 4 |
| P61* | 113 | 21 | 4 |
| P4 | 116 | 14 | 3-4 |
| P11 | 115 | 20 | 3 |
| P17 | 116 | 18 | 3 |
| P25 | 115 | 14 | 3-4 |

Comparison of the Blue Baking Varnishes JC1-B3 (Blue)

| Synthesis name | Gloss 20° | Haze | Transparency/color intensity |
|---|---|---|---|
| P59* | 115 | 21 | 4 |
| P60* | 112 | 38 | 3 |
| P61* | 114 | 27 | 3-4 |
| P4 | 115 | 26 | 2 |
| P11 | 116 | 27 | 1 |
| P17 | 115 | 24 | 3 |
| P25 | 117 | 20 | 2 |

The dispersing additives of the invention P4, P11, P17 and P25 exhibit lower haze, better gloss values and higher transparency and color intensity compared to the prior art P59*, P60* and P61* for pigment concentrates based on Laropal A81 used in an s acid-catalyzed baking varnish.

The invention claimed is:

1. A reaction product containing amido amine groups, comprising one or more species of general formula (I)

$$(R^1-X)_p-Z^1-(XH)_y \quad (I)$$

where p+y=w and
w is an integer from 1 to 10,
p is an integer from 1 to 10,
y is an integer from 0 to 9, and
X is O, and XH is a hydroxyl group OH,
where p+y<10, and
the p $R^1$ radicals are independently a radical of general formula (II)

$$Y-O-CO-NH-R^2-NH-CO \quad (II)$$

in which the p Y radicals are independently a branched or unbranched, saturated or unsaturated organic radical which has 1 to 1000 carbon atoms and does not contain any hydroxyl groups, any primary amino groups or any secondary amino groups,
the p $R^2$ radicals are independently a branched or unbranched, saturated or unsaturated organic radical having 6 to 20 carbon atoms, and
$Z^1$ is a branched or unbranched, saturated or unsaturated organic radical containing at least two carbon atoms, having at least one amide group and at least one tertiary amino group.

2. The reaction product containing amido amine groups as claimed in claim 1, containing at least 40% by weight of one or more species of the general formula (I).

3. The reaction product containing amido amine groups as claimed in claim 1, wherein a species of general formula (IV) which is free of urethane groups, is reactive toward isocyanate groups and is a reactant for the reaction product comprising one or more species of the formula (I)

$$(HX)_p-Z^1-(HX)_y \quad (IV)$$

with p, y, X and $Z^1$ as defined for the general formula (I), wherein the species of general formula (IV) is obtained by reacting one or more components A with one or more components B, one or more components C, or one or more components B and C, wherein
component A is selected from the group of ethylenically unsaturated carboxylic acids, esters thereof and acid halides thereof, where at least one C=C double bond and at least one C=O double bond are in conjugated form and the C=O double bond is selected from the group of the carboxylic acids, the carboxylic esters and the carbonyl halides;
component B is of general formula (V)

$$(R^3)_x-HN-(R^4)_z \quad (V)$$

where x+z=2 and
x is an integer from 0 to 2,
z is an integer from 0 to 2, and
$R^3$ is independently H or a branched or unbranched, saturated or unsaturated organic radical having 1 to 12 carbon atoms, and
$R^4$ is independently a branched or unbranched, saturated or unsaturated organic radical having 2 to 12 carbon atoms and 1 to 3 tertiary amino groups; and
component C is of general formula (VI)

$$(R^5)_k-HN-(R^6)_n \quad (VI)$$

where k+n=2 and
k is an integer from 0 to 1,
n is an integer from 1 to 2, and
$R^5$ is H or a branched or unbranched, saturated or unsaturated organic radical having 1 to 12 carbon atoms, and
$R^6$ is independently a branched or unbranched, saturated or unsaturated organic radical having 2 to 12 carbon atoms and 1 to 4 hydroxyl groups.

4. The reaction product containing amido amine groups as claimed in claim 3, wherein component A is an ethylenically unsaturated carboxylic ester.

5. The reaction product containing amido amine groups as claimed in claim 1, wherein Y contains at least one polyether radical, polyester radical, hydrocarbyl radical, polysiloxane radical, or mixtures thereof.

6. A process for preparing the reaction product containing amido amine groups as claimed in claim 3, wherein
i) at least one diisocyanate $R^2(NCO)_2$ is reacted with at least one monoalcohol Y—OH to form a urethane of general formula (III)

$$Y-O-CO-NH-R^2-NCO \quad (III)$$

ii) p urethanes of the general formula (III) are reacted to give a reaction product containing amido amine groups, comprising one or more species of the general formula (I)

$$(R^1-X)_p-Z^1-(XH)_y \quad (I)$$

and
wherein step ii) is conducted in one stage ii-a) or in a stage sequence ii-b),
in stage ii-a) p urethanes of the general formula (III) are reacted with a species of the general formula (IV) which is free of urethane groups and reactive toward isocyanate groups, and
in stage ii-b) p urethanes of the general formula (III) are reacted with an intermediate I containing at least one HX group reactive toward isocyanate groups with X as defined for the general formula (I) to form an intermediate J, wherein I is a Michael addition product of at least one component A with a component B or C, and then the intermediate J formed is reacted in an amidation reaction with a component B or C.

7. The process as claimed in claim 6, wherein the diisocyanate $R^2(NCO)_2$ is used in step i) relative to the monoalcohol Y—OH in a molar ratio of at least 1.1:1.0 and the diisocyanate $R^2(NCO)_2$ that has not been converted to the urethane of the general formula (III) in step i) is removed from the reaction mixture, optionally by distillation, prior to the performance of step ii).

8. The process as claimed in claim 6, wherein the diisocyanate $R^2(NCO)_2$ corresponding to the $R^2$ radical has two isocyanate groups of different reactivity.

9. The process as claimed in claim 8, wherein the diisocyanate $R^2(NCO)_2$ is selected from the group consisting of toluene 2,4-diisocyanate and isophorone diisocyanate.

10. A wetting agent and dispersant comprising the reaction product containing amido amine groups, as claimed in claim 1.

11. A composition comprising the reaction product containing amido amine groups, as claimed in claim 1.

12. A method of utilizing the reaction product containing amido amine groups as claimed in claim 1, comprising adding the reaction product as a wetting agent or dispersant or dispersion stabilizer or viscosity reducer or compatibilizer in coatings, varnishes, plastics, pigment pastes, sealants, cosmetics, ceramics, adhesives, potting compounds, spackling compounds, printing inks or other inks.

13. A reaction product containing amido amine groups which is one species of the general formula (I) of the reaction product as claimed in claim 1.

14. A reaction product containing amido amine groups, comprising one or more salt(s), one or more quaternization product(s), or one or more salts and one or more quaternization products of the species of the general formula (I) of the reaction product as claimed in claim 1.

15. A reaction product containing amido amine groups, comprising one or more modification products of the species of the general formula (I) of the reaction product as claimed in claim 1, wherein at least one of a) the one or more tertiary amino groups of the general formula (I) have been converted to amine oxides with oxygen, peroxo compounds or mixtures thereof, or b) XH groups still present in the general formula (I) have been reacted with carboxylic anhydrides.

16. The reaction product containing amido amine groups as claimed in claim 1, containing at least at least 90% by weight of one or more species of the general formula (I).

17. A wetting agent and dispersant comprising the reaction product containing amido amine groups, prepared by the process as claimed in claim 6.

18. A composition comprising the reaction product containing amido amine groups, prepared by the process as claimed in claim 6.

19. A method of utilizing the reaction product containing amido amine groups prepared by the process as claimed in claim 6, comprising adding the reaction product as a wetting agent or dispersant or dispersion stabilizer or viscosity reducer or compatibilizer in coatings, varnishes, plastics, pigment pastes, sealants, cosmetics, ceramics, adhesives, potting compounds, spackling compounds, printing inks or other inks.

\* \* \* \* \*

UNITED STATES PATENT AND TRADEMARK OFFICE
CERTIFICATE OF CORRECTION

PATENT NO. : 10,544,091 B2
APPLICATION NO. : 15/575128
DATED : January 28, 2020
INVENTOR(S) : Andreas Okkel et al.

It is certified that error appears in the above-identified patent and that said Letters Patent is hereby corrected as shown below:

In the Claims

Claim 1 at Column 35, Line 41 should read "where $p+y \leq 10$, and".

Signed and Sealed this
Twenty-fourth Day of March, 2020

Andrei Iancu
*Director of the United States Patent and Trademark Office*